United States Patent
Chen et al.

(10) Patent No.: US 12,234,282 B2
(45) Date of Patent: *Feb. 25, 2025

(54) THERAPY FOR GLAUCOMA AND OPTIC NEUROPATHY BY TARGETING COLONY STIMULATING FACTORS

(71) Applicant: The Schepens Eye Research Institute, Inc., Boston, MA (US)

(72) Inventors: Dong Feng Chen, Newtonville, MA (US); Ji Min, Boston, MA (US); Kin-Sang Cho, Boston, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/318,336

(22) Filed: May 16, 2023

(65) Prior Publication Data

US 2024/0025986 A1    Jan. 25, 2024

Related U.S. Application Data

(63) Continuation of application No. 16/977,783, filed as application No. PCT/US2019/020787 on Mar. 5, 2019, now Pat. No. 11,692,029.

(60) Provisional application No. 62/638,884, filed on Mar. 5, 2018.

(51) Int. Cl.
| | |
|---|---|
| A61K 39/395 | (2006.01) |
| A61K 9/00 | (2006.01) |
| A61K 38/19 | (2006.01) |
| C07K 16/24 | (2006.01) |
| C07K 16/28 | (2006.01) |
| A61K 45/06 | (2006.01) |

(52) U.S. Cl.
CPC .......... *C07K 16/243* (2013.01); *A61K 9/0048* (2013.01); *A61K 38/193* (2013.01); *C07K 16/2866* (2013.01); *A61K 39/395* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 7,884,069 B2 | 2/2011 | Schaebitz et al. | |
| 11,692,029 B2 * | 7/2023 | Min | A61P 27/06 424/158.1 |
| 2010/0112038 A1 | 5/2010 | Schaebitz et al. | |
| 2015/0158950 A1 | 6/2015 | Dimoudis et al. | |

FOREIGN PATENT DOCUMENTS

| | | |
|---|---|---|
| EP | 3050570 | 8/2016 |
| JP | 2018-501254 | 1/2018 |
| WO | WO 2004/060265 | 7/2004 |
| WO | WO 2005/048914 | 6/2005 |
| WO | WO 2006/008582 | 1/2006 |
| WO | WO 2011/119773 | 9/2011 |
| WO | WO 2014/036357 A1 | 3/2014 |
| WO | WO 2016/183296 | 11/2016 |
| WO | WO 2017/162884 | 9/2017 |
| WO | WO 2018/182527 | 10/2018 |

OTHER PUBLICATIONS

Albert et al., "Preclinical activity of ABT-869, a multitargeted receptor tyrosine kinase inhibitor," Mol Cancer Ther., 2006, 5(4):995-1006.
Andre et al., "Targeting FGFR with Dovitinib (TKI258): Preclinical and Clinical Data in Breast Cancer," Clin Cancer Res., 2013, 19(13):3693-702.
Ashman et al., "Therapeutic targeting of c-KIT in cancer," Expert Opin Investig Drugs, 2013, 22(1):103-15.
Blay et al., "Nilotinib: a novel, selective tyrosine kinase inhibitor," Semin Oncol., 2011, 38(Suppl 1):S3-9.
Cannarile et al., "Colony-stimulating factor 1 receptor (CSF1R) inhibitors in cancer therapy," J Immunother Cancer, 2017, 5(1):53, 13 pages.
CreativeBioLabs.net [online], "Agonistic Antibody," 2022, retrieved on Dec. 15, 2022, retrieved from URL<https://www.creativebiolabs.net/agonistic-antibody_72.htm>, 6 pages.
Cueva Vargas et al., "The glial cell modulator ibudilast attenuates neuroinflammation and enhances retinal ganglion cell viability in glaucoma through protein kinase A signaling," Neurobiology of Disease, Sep. 2016, 93:156-171.
Ebneter et al., "Dramatic effect of oral CSF-1R kinase inhibitor on retinal microglia revealed in vivo scanning laser ophthalmoscopy," Translational Vision Science & Technology, Apr. 2017, 6(2):10, 4 pages.
Extended European Search Report in European Appln No. 19764092.3, dated Apr. 12, 2022, 18 pages.
Extended European Search Report in European Appln No. 19764092.3, dated Nov. 30, 2021, 16 pages.
Gerber et al., "CSF1R Inhibition Reduces Microglia Proliferation, Promotes Tissue Preservation and Improves Motor Recovery After Spinal Cord Injury," Front Cell Neurosci., 2018, 12:368, 17 pages.
Hayreh, "Ischaemic optic neuropathy," Indian J Opthalmol, 2000, 48:171-194.
Hexner et al., "Lestaurtinib (CEP701) is a JAK2 inhibitor that suppresses JAK2/STAT5 signaling and the proliferation of primary erythroid cells from patients with myeloproliferative disorders," Blood, 2008, 111(12):5663-71.
Hotta and Fujiki, "Recent Topics in Optic Neuropathy—Neurological diseases, from an ophthalmologist's perspective," Juntendo Medicine, 1999, 45(3):315-321, 9 pages (with English abstract).
International Preliminary Report on Patentability in International Appln. No. PCT/US2019/020787, dated Sep. 17, 2020, 11 pages.
International Search Report and Written Opinion in International Appln. No. PCT/US2019/020787, dated Sep. 17, 2019, 14 pages.

(Continued)

*Primary Examiner* — Elizabeth C. Kemmerer
(74) *Attorney, Agent, or Firm* — Fish & Richardson P.C.

(57) ABSTRACT

The invention provides compositions and methods for treating optic neuropathic disorders.

18 Claims, 16 Drawing Sheets

Specification includes a Sequence Listing.

(56) References Cited

OTHER PUBLICATIONS

Ji et al., "Regulation of microglia activation by CSFs drives neurodegeneration in glaucoma," Abstract, Presented at ARVO Annual Meeting, Honolulu, HI, Apr. 29-May 3, 2018; Investigative Ophthalmology & Visual Science, Jul. 2018, 59:2014, 2 pages.
Kahloun et al., "Abstract: Infectious optic neuropathies: A clinical update," Eye and Brain, 2015, 7:59-81 (Abstract Only).
Kitagawa et al., "Characterization of kinase inhibitors using different phosphorylation states of colony stimulating factor-L receptor tyrosine kinase," Journal of Biochemistry, Jan. 2012, 151(1):47-55.
Kothiwale et al., "Discoidin domain receptor 1 (DDR1) kinase as target for structure-based drug discovery," Drug Discov Today, 2015, 20(2):255-61.
Kumaran et al., "Traumatic Optic Neuropathy: A Review," Craniomaxillofacial Trauma and Reconstruction, 2015, 8(1):31-41.
Lesca et al., "Structural Analysis of the Human Fibroblast Growth Factor Receptor 4 Kinase," J Mol Biol., 2014, 426(22):3744-3756.
Liddelow et al., "Neurotoxic Reactive Astrocytes are Induced by Activated Microglia," Nature, 2017, 541(7638):481-487.
Lyons et al., "Macrophage depletion through colony stimulating factor 1 receptor pathway blockade overcomes adaptive resistance to anti-VEGF therapy," Oncotarget, 2017, 8(57):96496-96505.
Murone et al., "Debio 0617B Inhibits Growth of STAT3-Driven Solid Tumors through Combined Inhibition of JAK, SRC, and Class III/V Receptor Tyrosine Kinases," Mol Cancer Ther., 2016, 15(10):2334-2343.
Office Action in Japanese Appln. No. 2020-546441, dated Mar. 23, 2023, 12 pages (with English translation).
Office Action in Japanese Appln. No. 2020-546441, dated Sep. 13, 2023, 7 pages (with English translation).
Ohno et al., "A c-fms tyrosine kinase inhibitor, Ki20227, suppresses osteoclast differentiation and osteolytic bone destruction in a bone metastasis model," Mol Cancer Ther., 2006, 5(11):2634-43.
Petzold et al., "Diagnosis and classification of autoimmune optic neuropathy," Autoimmunity Reviews, 2014, 13:539-545.
Pitiot et al., "Alternative Routes of Administration for Therapeutic Antibodies-State of the Art," Antibodies, Aug. 2022, 11(3):56, 25 pages.
Pyonteck et al., "CSF-1R inhibition alters macrophage polarization and blocks glioma progression," Nat Med., 2013, 19(10):1264-72.
Ramirez et al., "The Role of Microglia in Retinal Neurodegeneration: Alzheimer's Disease, Parkinson, and Glaucoma," Front. Aging Neurosci., Jul. 2017, 9:214, 21 pages.
Ries et al., "Targeting tumor-associated macrophages with anti-CSF-1R antibody reveals a strategy for cancer therapy," Cancer Cell, 2014, 25(6):846-59.
Ryder et al., "Genetic and Pharmacological Targeting of CSF-1/CSF-1R Inhibits Tumor-Associated Macrophages and Impairs BRAF-Induced Thyroid Cancer Progression," PLoS One, 2013, 8(1):e54302, 10 pages.
Schallenberg et al., "GM-CSF Regulates the ERK 1/2 Pathways and Protects Injured Retinal Ganlion Cells from Induced Death," Experimental Eye Research, 2009, 89(5):665-77.
Smith et al., "Characterizing and Overriding the Structural Mechanism of the Quizartinib-Resistant FLT3 'Gatekeeper' F691L Mutation with PLX3397," Cancer Discov., 2015, 5(6):668-79.
Smith et al., "The highly specific CSF1R inhibitor DCC-3014 exhibits immunomodulatory and anti-invasive activities in cancer models," Poster, Presented at Proceedings: AACR 107th Annual Meeting 2016, New Orleans, LA, Apr. 16-20, 2016; Cancer Res, 2016, 76(14 Suppl):4889, 1 page.
Subbiah et al., "Next generation sequencing analysis of platinum refractory advanced germ cell tumor sensitive to Sunitinib (Sutent®) a VEGFR2/PDGFRβ/c-kit/ FLT3/RET/CSF1R inhibitor in a phase II trial," J Hematol Oncol., 2014, 7:52, 10 pages.
Tahmasebi et al., "Effect of the CSF1R inhibitor PLX3397 on remyelination of corpus callosum in a cuprizone-induced demyelination mouse model," J Cell Biochem., 2019, 11 pages.
Takashima, "Current Status and Challenges of Drug Delivery to the Retina," Journal of Pharmaceutical Science and Technology, Japan, 2012, 72(2):117-121, 9 pages (with English translation).
Ullrich et al., "BAY 43-9006/Sorafenib blocks CSF1R activity and induces apoptosis in various classical Hodgkin lymphoma cell lines," Br J Haematol., 2011, 155(3):398-402.
Von Tresckow et al., "An Open-Label, Multicenter, Phase I/II Study of JNJ-40346527, a CSF-IR Inhibitor, in Patients with Relapsed or Refractory Hodgkin Lymphoma," Clin Cancer Res., 2015, 21(8):1843-50.
Yamaura et al., "A novel irreversible FLT3 inhibitor, FF-10101, shows excellent efficacy against AML cells with FLT3 mutations," Blood, 2018, 131(4):426-438.
Zhou et al., "CS2164, a novel multi-target inhibitor against tumor angiogenesis, mitosis and chronic inflammation with anti-tumor potency," Cancer Sci., 2017, 108(3):469-477.
Masek-Hammerman et al., "Monoclonal antibody against macrophage colony-stimulating factor suppresses circulating monocytes and tissue macrophage function but does not alter cell infiltration/activation in cutaneous lesions or clinical outcomes in patients with cutaneous lupus erythematosus," Clinical and Experimental Immunology, 2015, 183(2):258-270.
Notice of Allowance in Japanese Appln. No. 2020-546441, dated Mar. 5, 2024, 6 pages (with English translation).
Office Action in Chinese Appln. No. 201980030208.9, dated Dec. 1, 2023, 18 pages (with English translation).
Office Action in Australian Appln. No. 2019232730, dated Jul. 30, 2024, 7 pages.
Office Action in Chinese Appln. No. 201980030208.9, dated Jun. 26, 2024, 8 pages (with English translation).
Office Action in European Appln. No. 19764092.3, mailed Sep. 24, 2024, 8 pages.

* cited by examiner

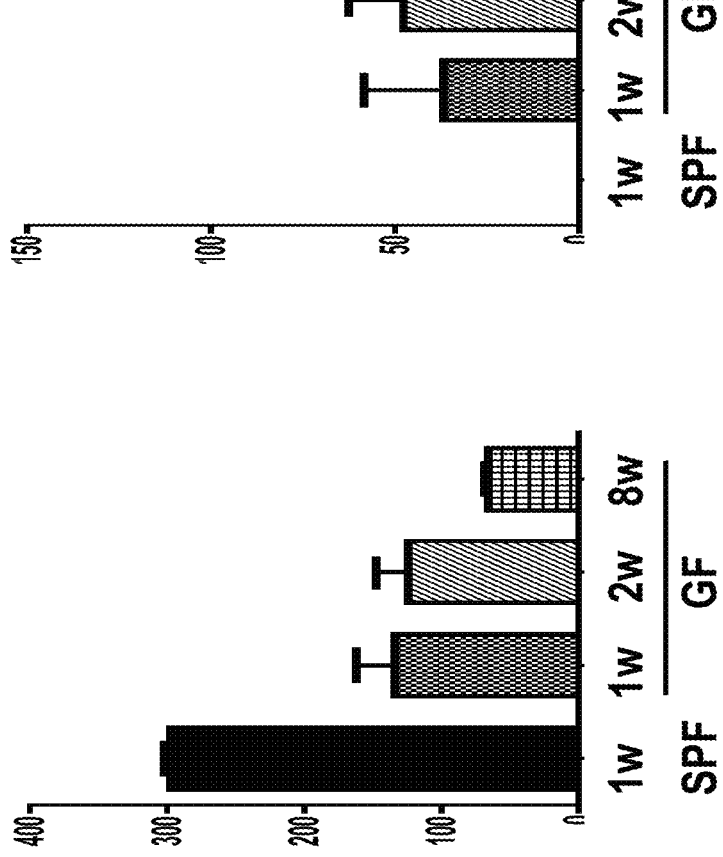
FIG. 4A / FIG. 4B

Upregulated CSF1/CSF1R expression in microbead (MB)-injected mice

```
                              SEQUENCE LISTING

Sequence total quantity: 4
SEQ ID NO: 1            moltype = AA   length = 554
FEATURE                 Location/Qualifiers
source                  1..554
                        mol_type = protein
                        organism = Homo sapiens
SEQUENCE: 1
MTAPGAAGRC PPTTWLGSLL LLVCLLASRS ITEEVSEYCS HMIGSGHLQS LQRLIDSQME   60
TSCQITFEFV DQEQLKDPVC YLKKAFLLVQ DIMEDTMRFR DNTPNAIAIV QLQELSLRLK  120
SCFTKDYEEH DKACVRTFYE TPLQLLEKVK NVFNETKNLL DKDWNIFSKN CNNSFAECSS  180
QDVVTKPDCN CLYPKAIPSS DPASVSPHQP LAPSMAPVAG LTWEDSEGTE GSSLLPGEQP  240
LHTVDPGSAK QRPPRSTCQS FEPPETPVVK DSTIGGSPQP RPSVGAFNPG MEDILDSAMG  300
TNWVPEEASG EASEIPVPQG TELSPSRPGG GSMQTEPARP SNFLSASSPL PASAKGQQPA  360
DVTGTALPRV GPVRPTGQDW NHTPQKTDHP SALLRDPPEP GSPRISSLRP QGLSNPSTLS  420
AQPQLSRSHS SGSVLPLGEL EGRRSTRDRR SPAEPEGGPA SEGAARPLPR FNSVPLTDTG  480
HERQSEGSFS PQLQESVFHL LVPSVILVLL AVGGLLFYRW RRRSHQEPQR ADSPLEQPEG  540
SPLTQDDRQV ELPV                                                    554

SEQ ID NO: 2            moltype = AA   length = 972
FEATURE                 Location/Qualifiers
source                  1..972
                        mol_type = protein
                        organism = Homo sapiens
SEQUENCE: 2
MGPGVLLLLL VATAWHGQGI PVIEPSVPEL VVKPGATVTL RCVGNGSVEW DGPPSPHWTL   60
YSDGSSSILS TNNATFQNTG TYRCTEPGDP LGGSAAIHLY VKDPARPWNV LAQEVVVFED  120
QDALLPCLLT DPVLEAGVSL VRVRGRPLMR HTNYSFSPWH GFTIHRAKFI QSQDYQCSAL  180
MGGRKVMSIS IRLKVQKVIP GPPALTLVPA ELVRIRGEAA QIVCSASSVD VNFDVFLQHN  240
NTKLAIHQQS DFHNNRYQKV LTLNLDQVDF QHAGNYSCVA SNVQGKHSTS MFFRVVESAY  300
LNLSSEQNLI QEVTVGEGLN LKVMVEAYPG LQGFNWTYLG PFSDHQPEPK LANVTTKDTY  360
RHTFTLSLPR LKPSEAGRYS FLARNPGGWR ALTFELTLRY PPEVSVIWTF INGSGTLLCA  420
ASGYPQPNVT WLQCSGHTDR CDEAQVLQVW DDPYPEVLSQ EPFHKVTVQS LLTVETLEHN  480
QTYECRAHNS VGSGSWAFIP ISAGAHTHPP DEFLFTPVVV ACMSIMALLL LLLLLLLYKY  540
KQKPKYQVRW KIIESYEGNS YTFIDPTQLP YNEKWEFPRN NLQFGKTLGA GAFGKVVEAT  600
AFGLGKEDAV LKVAVKMLKS TAHADEKESL MSELKIMSHL GQHENIVNLL GACTHGGPVL  660
VITEYCCYGD LLNFLRRKAE AMLGPSLSPG QDPEGGVDYK NIHLEKKYVR RDSGFSSQGV  720
DTYVEMRPVS TSSNDSFSEQ DLDKEDGRPL ELRDLLHFSS QVAQGMAFLA SKNCIHRDVA  780
ARNVLLTNGH VAKIGDFGLA RDIMNDSNYI VKGNARLPVK WMAPESIFDC VYTVQSDVWS  840
YGILLWEIFS LGLNPYPGIL VNSKFYKLVK DGYQMAQPAF APKNIYSIMQ ACWALEPTHR  900
PTFQQICSFL QEQAQEDRRE RDYTNLPSSS RSGGSGSSSS ELEEESSSEH LTCCEQGDIA  960
QPLLQPNNYQ FC                                                      972

SEQ ID NO: 3            moltype = DNA   length = 3904
FEATURE                 Location/Qualifiers
source                  1..3904
                        mol_type = genomic DNA
                        organism = Homo sapiens
SEQUENCE: 3
ggtggccttg cctagctaaa aggggaagaa gaggatcagc ccaaggagga ggaagaggaa   60
aacaagacaa acagccagtg cagaggagag gaacgtgtgt ccagtgtccc gatccctgcg  120
gagctagtag ctgagagctc tgtgcccctgg gcaccttgca gccctgcacc tgcctgccac  180
```

```
ttccccaccg aggccatggg cccaggagtt ctgctgctcc tgctggtggc cacagcttgg    240
catggtcagg gaatcccagt gatagagccc agtgtccccg agctggtcgt gaagccagga    300
gcaacggtga ccttgcgatg tgtgggcaat ggcagcgtgg aatgggatgg cccccccatca   360
cctcactgga ccctgtactc tgatggctcc agcagcatcc tcagcaccaa caacgctacc    420
ttccaaaaca cggggaccta tcgctgcact gagcctggag acccctggg aggcagcgcc     480
gccatccacc tctatgtcaa agaccctgcc cggcctggga acgtgctagc acaggaggtg    540
gtcgtgttcg aggaccagga cgcactactg ccctgtctgc tcacagaccc ggtgctgaaa   600
gcaggcgtct cgctggtgcg tgtgcgtggc cggcccctca tgcgccacac caactactcc    660
ttctcgccct ggcatggctt caccatccac agggccaagt tcattcagag ccaggactat    720
caatgcagtg ccctgatggg tggcaggaag gtgatgtcca tcagcatccg gctgaaagtg    780
cagaaagtca tcccagggcc cccagccttg acactggtgc ctgcagagct ggtgcggatt    840
cgagggaggg ctgcccagat cgtgtgctca gccagcagtg ttgatgttaa ctttgatgtc    900
ttcctccaac acaacaacac caagctcgca atccatcaac aatctgactt tcataataac    960
cgttaccaaa aagtcctgac cctcaacctc gatcaagtag atttccaaca tgccggcaac   1020
tactcctgcg tggccagcaa cgtgcagggc aagcactcca cctccatgtt cttccggggtg   1080
gtagagagtg cctacttgaa cttgagctct gagcagaacc tcatccagga ggtgaccgtg   1140
ggggaggggc tcaacctcaa agtcatggtg gaggcctacc caggcctgca aggttttaac    1200
tggacctacc tgggaccctt ttctgaccac cagcctgagc ccaagcttgc taatgttacc   1260
accaaggaca catacaggca caccttcacc ctctctctgc cccgcctgaa gccctctgag    1320
gctgccgct actccttcct ggccagaaac ccaggaggct ggagagctct gacgtttgag     1380
ctcacccttc gataccccc agaggtaagc gtcatatgga cattcatcaa cggctctggc    1440
accctttgt gtgctgcctc tgggtacccc cagcccaacg tacatggct gcagtgcagt     1500
ggccacactg ataggtgtga tgaggcccaa gtgctgcagg tctgggatga cccatcccct   1560
gaggtcctga gccaggagcc cttccacaag gtgacggtgc agagcctgct gactgttgag    1620
accttagagc acaaccaaac ctacgagtgc agggcccaca cagcgtggg gagtggctcc    1680
tgggccttca tacccatctc tgcaggagcc cacacgcatc cccgatgcag ttcctcttc    1740
acaccagtgg tggtcgcctg catgtccatc atggcctttgc tgtgctgctg gctcctgctg   1800
ctattgtaca agtataagca gaagcccaag taccaggtcc gctggaagat catcgagagc   1860
tatgagggca cagttatac tttcatcgac cccacgcagc tgccttacaa cgagaagtgg    1920
gagttccccc ggaacaacct gcagtttggt aagaccctcg gagctggagc ctttgggaag   1980
gtggtggagg ccacggcctt tggtctgggc aaggaggatg ctgtcctgaa ggtggctgtg    2040
aagatgctga agtccacggc ccatgctgat gagaaggagt cccctcatgtc cgagctgaag    2100
atcatgagcc acctgggcca gcacgagaac atcgtcaacc ttctgggaac ctgtacccat   2160
ggaggccctg tactggtcat cacggagtac tgttgctatg gcgacctgct caactttctg   2220
cgaaggaagc ctgaggccat gctgggaccc agcctgagcc ccggcaggga ccccgaggga   2280
ggcgtcgact ataagaacat ccacctcgag aagaatatg tccgcaggga cagtggcttc   2340
tccagccagg gtgtggacac ctatgtggag atgaggcctg tctccacttc ttcaaatgac   2400
tccttctctg agcaagacct ggacaaggag gatggacggc ccggacctg aaggggacctg    2460
cttcacttct ccagccaagt agcccagggc atggccttcc tcgcttccaa gaattgcatc    2520
caccgggacg tggcagcgcg taacgtgctg ttgaccaatg tcatgtggc caagattggg    2580
gacttcgggc tggctaggga catcatgaat gactccaact acattgtcaa gggcaatgcc    2640
cgcctgcctg tgaagtggat ggccccagag agcatctttg actgtgtcta cacggttcag    2700
agcgacgtct ggtcctatgg catcctcctc tgggagatct tctcacttgg gtgaatccc   2760
taccctggca tcctggtgaa cagcaagttc tataaactgg tgaaggatgg ataccaaatg   2820
gcccagcctg catttgcccc aaagaatata tacagcatca tgcaggcctg ctgggccttg    2880
gagcccaccc acagacccac cttccagcag atctgctcct tccttcagga gcaggccaa    2940
gaggacagga gagagcggga ctataccaat ctgccgagca gcagcagaag cggtggcagc   3000
ggcagcagca gcagtgagct ggaggaggag agctctagtg agcacctgac ctgctgcgag   3060
caagggggata tcgcccagcc cttgctgcag cccaacaact atcagttctg ctgaggagtt    3120
gacgacaggt agtaccactc tcccctcctc caaacttcaa ctcctccatg gatggggcga    3180
cacggggaga acatacaaac tctgcctttcg gtcatttcac tcaacagctc ggcccagctc   3240
tgaaacttgg gaaggtgagg gattcaggg aggtcagagg atcccacttc ctgagcatgg    3300
gccatcactg ccagtcaggg cctgggggct gagccctcac cccccgcctc ccctactgtt   3360
ctcatggtgt tggcctcgtg tttgctatgc caactagtag aaccttcttt cctaatcccc   3420
ttatcttcat ggaaatggac tgactttatg cctatgaagt ccccaggagc tacactgata    3480
ctgagaaaac caggctcttt ggggctagca agactggcag agagtgagat ctccctctct   3540
gagaggagca gcagatgctc acagaccaca ctcagctcag gccccttgga gcaggatggc    3600
tcctctaaga atctcacagg acctcttagt ctctgcccta tacgccgcct tcactccaca    3660
gcctcacccc tcccacccc atactggtac tgctgtaatg agccaagtgg cagctaaaag    3720
ttggggtgt tctgcccagt cccgtcattc tgggctagaa ggcaggggac cttggtcagt    3780
ggctggccac accaagcagg aagcacaaac tcccccaagc tgactcatcc taactaacag   3840
tcacgccgtg ggatgtctct gtccacatta aactaacagc attaatacaa aaaaaaaaa    3900
aaaa                                                                  3904

SEQ ID NO: 4            moltype = AA   length = 144
FEATURE                 Location/Qualifiers
source                  1..144
                        mol_type = protein
                        organism = Homo sapiens
SEQUENCE: 4
MWLQSLLLLG TVACSISAPA RSPSPSTQPW EHVNAIQEAR RLLNLSRDTA AEMNETVEVI    60
SEMFDLQEPT CLQTRLELYK QGLRGSLTKL KGPLTMMASH YKQHCPPTPE TSCATQIITF   120
ESFKENLKDF LLVIPFDCWE PVQE                                           144
```

THERAPY FOR GLAUCOMA AND OPTIC NEUROPATHY BY TARGETING COLONY STIMULATING FACTORS

CROSS-REFERENCE TO RELATED APPLICATIONS

The application is a continuation of U.S. patent application Ser. No. 16/977,783, now U.S. Pat. No. 11,692,029, filed Sep. 2, 2020, National Stage Application filed under 35 U.S.C. § 371, of International Patent Application No. PCT/US2019/020787, filed on Mar. 5, 2019, which claims the benefit of U.S. Provisional Application 62/638,884 filed on Mar. 5, 2018. The entire contents of which are incorporated by reference in their entirety.

STATEMENT AS TO FEDERALLY SPONSORED RESEARCH

This invention was made with government support under R01 EY025259 awarded by the National Eye Institute. The Government has certain rights in the invention.

SEQUENCE LISTING

This application contains a Sequence Listing that has been submitted electronically as an XML file named "00633-0302002_SL_ST26.XML." The XML file, created on May 15, 2023, is 10,065 bytes in size. The material in the XML file is hereby incorporated by reference in its entirety.

FIELD OF THE INVENTION

The present invention relates to ocular disorders.

BACKGROUND

Glaucoma is a group of ocular disorders associated with elevated intraocular pressure (TOP) and death of retinal ganglion cells (RGCs) and optic nerve degeneration. Glaucoma is a leading cause of irreversible blindness worldwide. Treatment options have been limited solely to lowering intraocular pressure (IOP), which slows down disease progression but does not halt the disease.

SUMMARY OF THE INVENTION

The invention provides compositions and methods that address a fundamental underlying defect in the cause of blindness (independent of or associated with high IOP).

Accordingly, a method for treating an optic neuropathic disorder in a subject is carried out by locally administering to the eye an inhibitor of colony stimulating factor-1 (CSF1) or a receptor thereof. For example, the inhibitor is an antibody. Alternatively, the method is carried out by locally administering to the eye a colony stimulating factor-2 (CSF2) protein or polypeptide.

The subject is diagnosed with glaucoma or is identified as being predisposed to or at risk of developing glaucoma, e.g., the subject does not yet exhibit elevated intraocular pressure (TOP). Thus, the compositions and methods are particularly valuable for early treatment for this disorder.

In certain embodiments, a method for treating an optic neuropathic disorder in a subject comprising locally administering to the eye an inhibitor of colony stimulating factor-1 (CSF1) or a receptor thereof or by locally administering to the eye a colony stimulating factor-2 (CSF2) protein or polypeptide. In certain embodiments, the subject is diagnosed with glaucoma. In certain embodiments, the inhibitor or polypeptide is administered intravitreally. In certain embodiments, the inhibitor comprises an antibody which specifically binds to CSF1 or a CSF1 receptor.

In certain embodiments, a method preventing or treating an optic neuropathic disorder in a subject comprising locally administering to the eye, a pharmaceutical composition comprising a therapeutically effective amount of an inhibitor of colony stimulating factor-1 (CSF1) or a receptor thereof and a colony stimulating factor-2 (CSF2) polypeptide, thereby preventing or treating the optic neuropathic disorder. In certain embodiments, the inhibitor of CSF1 or a receptor thereof and a CSF2 protein or polypeptide recombinant protein suppress microglial activation. In certain embodiments, the inhibitor of CSF1 or a receptor thereof and a CSF2 protein or polypeptide recombinant protein protect loss of retinal ganglion cells (RGCs) and vision function. In certain embodiments, the inhibitor of CSF1 or a receptor thereof and a CSF2 protein or polypeptide recombinant protein suppress microglial activation, protect the loss of retinal ganglion cells (RGCs) and vision function. In certain embodiments, the inhibitor of CSF1 or a receptor thereof, comprises antibodies, antibody fragments, aptamers, small molecules, antisense oligonucleotides, siRNA reagents, Fab, Fab', F(ab')$_2$ fragments, Fv fragments, single chain antibodies, antibody mimetics, peptoids, cytokines, cellular factors, enzymes or combinations thereof. In certain embodiments, the pharmaceutical composition comprises an anti-CSF1 antibody and a CSF2 recombinant peptide. In certain embodiments, the pharmaceutical composition comprises an anti-CSF1 receptor antibody and a CSF2 recombinant peptide. In certain embodiments, the pharmaceutical composition comprises an anti-CSF1 antibody and an anti-CSF1 receptor antibody. In certain embodiments, the pharmaceutical composition comprises an anti-CSF1 antibody, an anti-CSF1 receptor antibody and a CSF2 polypeptide. In certain embodiments, the pharmaceutical composition comprises an inhibitor of CSF1 antibody and/or an inhibitor of CSF1 receptor and/or a CSF2 polypeptide.

In certain embodiments, a pharmaceutical composition comprises a therapeutically effective amount of an inhibitor of colony stimulating factor-1 (CSF1) or a receptor thereof and a colony stimulating factor-2 (CSF2) protein or polypeptide. In certain embodiments, the inhibitor of CSF1 or a receptor thereof, comprises antibodies, antibody fragments, aptamers, small molecules, antisense oligonucleotides, siRNA reagents, Fab, Fab', F(ab')2 fragments, Fv fragments, single chain antibodies, antibody mimetics, peptoids, cytokines, cytokine agonists, cytokine antagonists, cellular factors, enzymes or combinations thereof.

In certain embodiments, a method of suppressing microglial activation in a subject, comprises administering to the subject an inhibitor of colony stimulating factor-1 (CSF1) or a receptor thereof or by locally administering to the eye a colony stimulating factor-2 (CSF2) protein or polypeptide. In certain embodiments, the subject is diagnosed with glaucoma. In certain embodiments, the CSF1 inhibitor, CSF1 receptor inhibitor or CSF2 polypeptide is administered intravitreally. In certain embodiments, the inhibitor of CSF1 or a receptor thereof, comprises antibodies, antibody fragments, aptamers, small molecules, antisense oligonucleotides, siRNA reagents, Fab, Fab', F(ab')2 fragments, Fv fragments, single chain antibodies, antibody mimetics, peptoids, cytokines, cytokine agonists, cytokine antagonists, cellular factors, enzymes or combinations thereof.

In certain embodiments, a CSF1 or CSF1 receptor inhibitors are formulated for ocular administration. In certain embodiments, a CSF1 inhibitor is formulated for ocular administration. In certain embodiments, a CSF2 polypeptide or protein formulated for ocular administration.

In some examples, the inhibitor or polypeptide is administered intravitreally. Exemplary inhibitors of CSF1 or CSF receptor include antibody specific for CSF1 or a CSF1 receptor. For example, a CSF1 inhibitor formulated for ocular administration.

Alternatively or in conjunction with CSF1 treatment, the therapy includes a CSF2 polypeptide or protein formulated for ocular administration.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Geribank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

DESCRIPTION OF THE DRAWINGS

FIGS. 4A and 4B are graphs showing the cytokine profiles in glaucomatous SPF and gem free mice. Quantification of serum levels of (FIG. 4A) colony stimulating factors 1 (CSF1) and (FIG. 4B) CSF2 in the retinas of specific pathogen free (SPF) and germ free (GF) mice at weeks 1, 2 and 8 after elevation of intraocular pressure (IOP), by Luminex assay. Note the consistent down-regulation of CSF1 and upregulation of CSF2 in the glaucomatous GF mice compared to SPF mice.

FIGS. 11A and 11 B are graphs demonstrating that visual function increased by treatment of CSF1RAb/CSF2 after MB injection. Assessment of vision contrast sensitivity and visual acuity in MB-induced glaucomatous mice received vehicle, CSF1RAb, CSF2 or CSF1RAb+CSF2 treatment at before (Ctr), 4 (G4w) and 6 (G4w) weeks after MB injection.

DETAILED DESCRIPTION

Figures 1A, 1B, 1C:
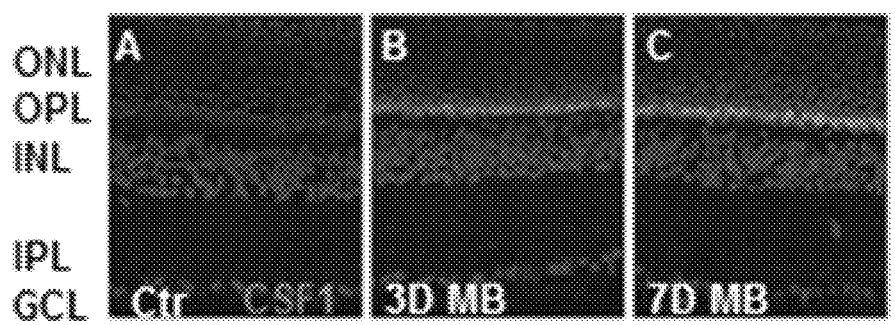
FIGS. 1A-1C are images of CSF1 expression on retinal sections of normal mice (FIG. 1A; Ctr) and mice at 3 (3D MB) and 7 (7D MB) days post microbead-injection (FIGS. 1B-1C, respectively).
Figure 1D:
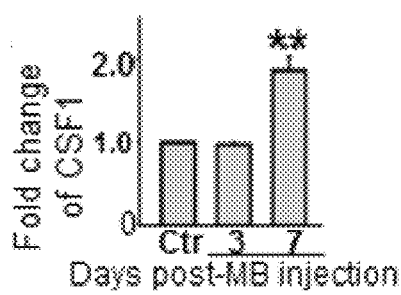
FIG. 1D is a bar graph showing relative fold change of CSF1 mRNA levels detected in the normal retina (Ctr) and retina taken from mice at 3 (3) and 7 (7) days post-microbead injection. Abbreviations: ONL (outer nuclear layer); OPL (outer plexiform layer; INL (inner nuclear layer); IPL (inner plexiform layer); GCL (ganglion cell layer). ** represents P value <0.001. These figures (FIGS. 1A-1D) show expression of CSF1 in normal and glaucomatous retina.
Figure 2A:
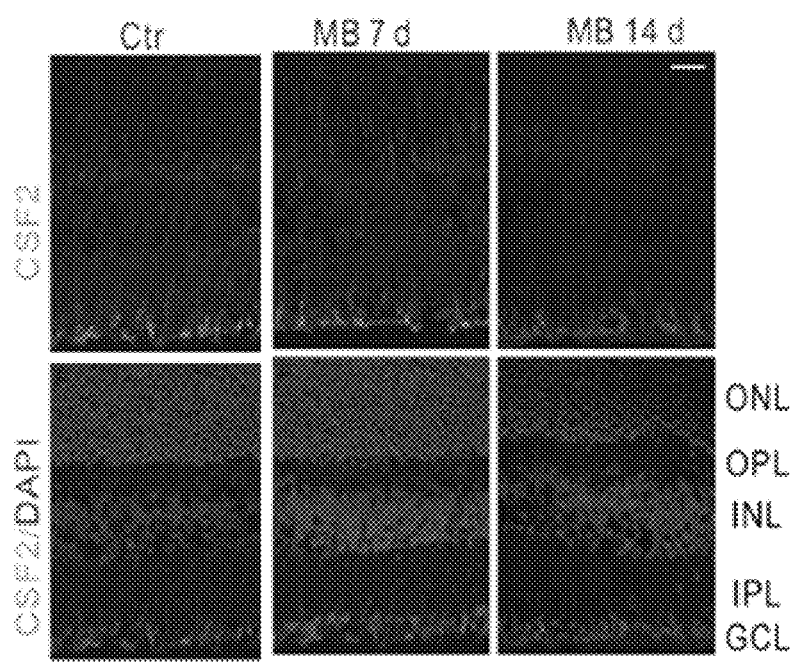
FIG. 2A is a series of representative images of retinal sections of normal (Ctr) and glaucomatous mice at 7 (MB 7D) and 14 (MB 14D) days post microbead injection.
Figure 2B:
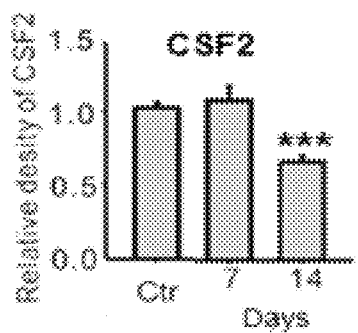
FIG. 2B is a bar graph showing quantification of CSF2 mRNA levels in control and the glaucomatous retinas determined by RT-PCR.
Figure 2C:
FIG. 2C is a photograph of the results of a representative Western blot showing the protein levels of CSF2 and β-actin as a loading control in the control and glaucomatous retinas.
Figure 2D:
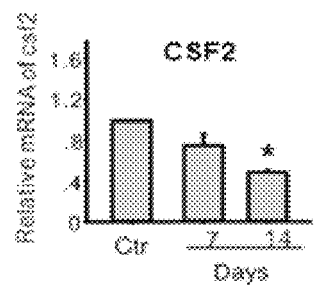
FIG. 2D is a bar graph showing quantification of CSF2 protein levels in normal and glaucomatous retinas at 7 and 14 days post-microbead injection that was normalized to the normal retina. * and *** represent P value <0.05 and 0.001. GCL=ganglion cell layer; IPL=inner plexiform layer; INL=inner nuclear layer; OPL=outer plexiform layer, and ONL=outer nuclear layer. These figures (FIGS. 2A-D) show expression of CSF2 in normal and glaucoma retina.
Figure 3A:
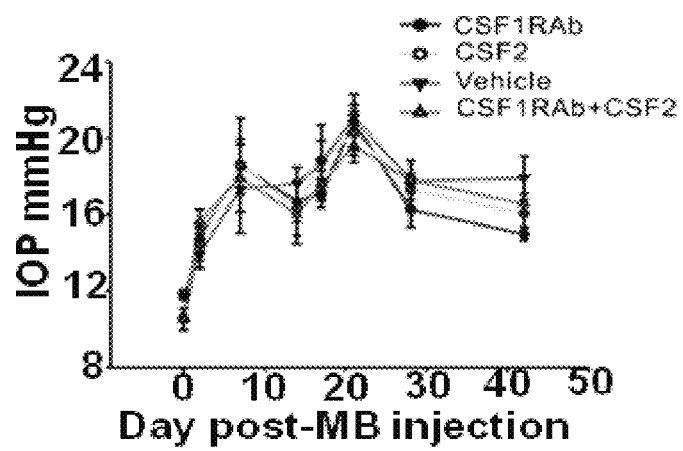
FIG. 3A is a line graph showing the intraocular pressure (IOP) level at baseline and up to 42 days/6 weeks post-MB injection of mice receiving either intravitreal injections of CSF1R Ab, CSF2, CSF1R Ab+CSF2 or control vehicle at D3 and D7.
Figure 3B:
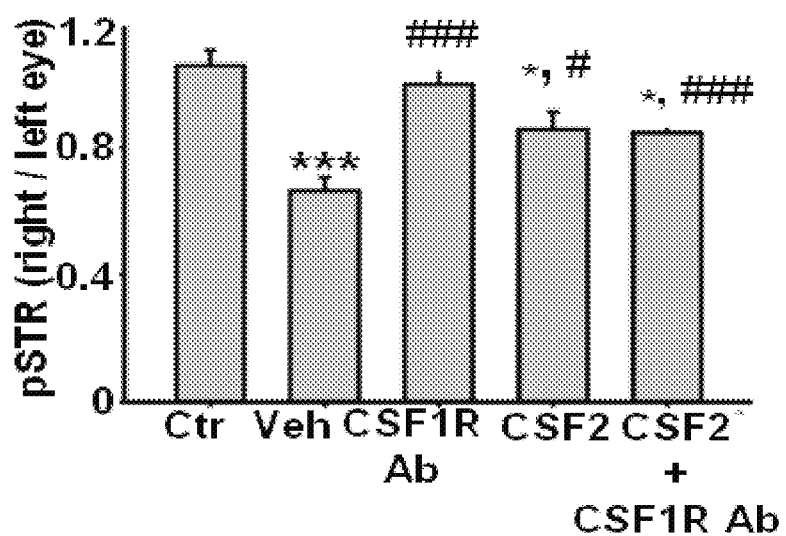
FIG. 3B is a bar graph showing the ratio of positive scotopic threshold response (pSTR) of glaucoma eye to contralateral normal eye.
Figure 3C:
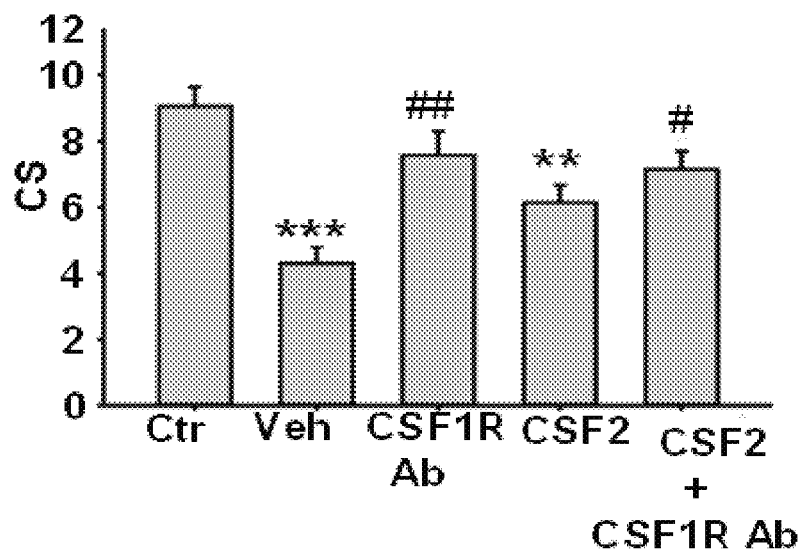
FIG. 3C is a bar graph showing the contrast sensitivity (CS) of the OMR.
Figure 3D:
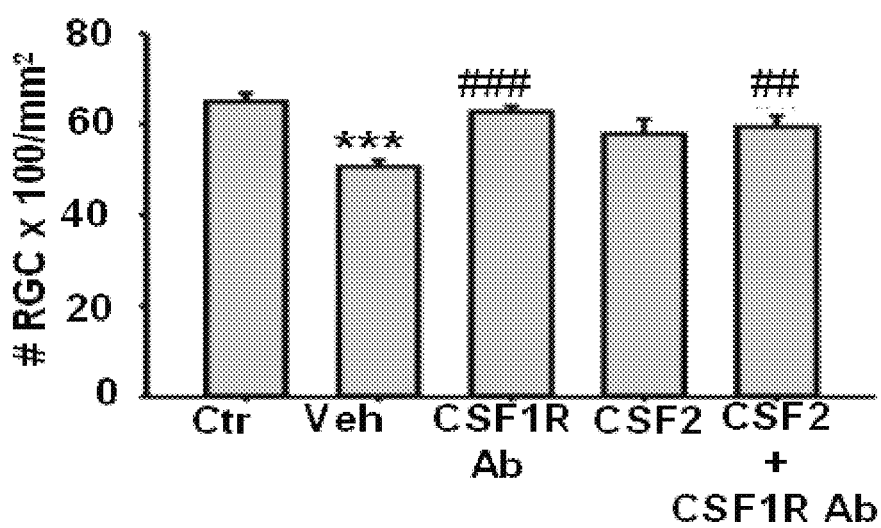
FIG. 3D is a bar graph showing Retinal Ganglion Cells (RGC) density of control (Ctr), vehicle (Veh) and CSF1R Ab, CSF2 and CSF2+CSF1 Ab-treated groups. Note Ctr group are the uninjured eyes.
Figure 3E:
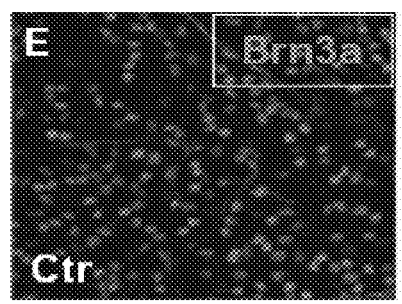
FIGS. 3E-3G are photomicrographs of Brn3a+ RGCs (red) at 6 week post-injection of microbeads. In these figures (FIGS. 3A-G), '#' and represents statistical analysis comparing to control and vehicle group, respectively. *,  and * represent P value <0.05, and 0.001, respectively. #, ## and ### represent P value <0.05, <0.01 and <0.001. These figures (FIGS. 3A-3G) demonstrate that modulating CSFs protects retinal function, visual performance and neuronal loss in an art-recognized mouse model (microbead-induced) of human glaucoma.
Figure 3F:
Figure 3G:
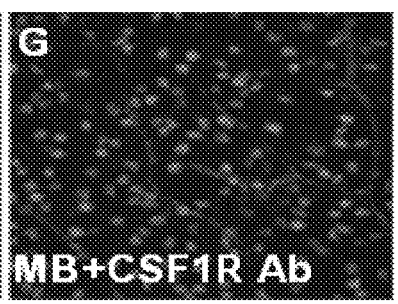
Figure 5A:
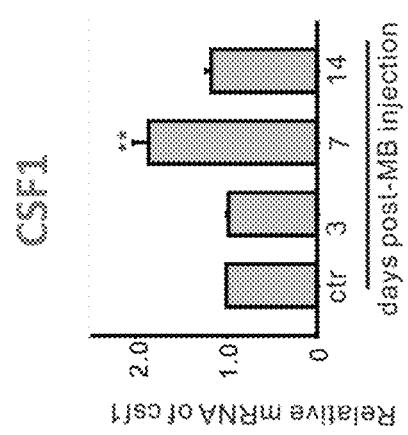
FIGS. 5A and 5B are graphs showing upregulated CSF1/CSF1R expression in microbead (MB)-injected mice. The results from qPCR quantification demonstrated upregulation of CSF1 (FIG. 5A) and CSF1R (FIG. 5B) expression in the mouse retinas after microbead-induced elevation of intraocular pressure.
Figure 5B:
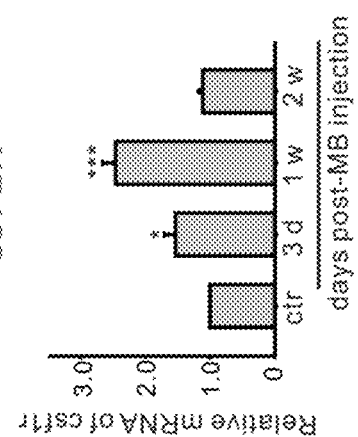
Figures 6A, 6B, 6C:
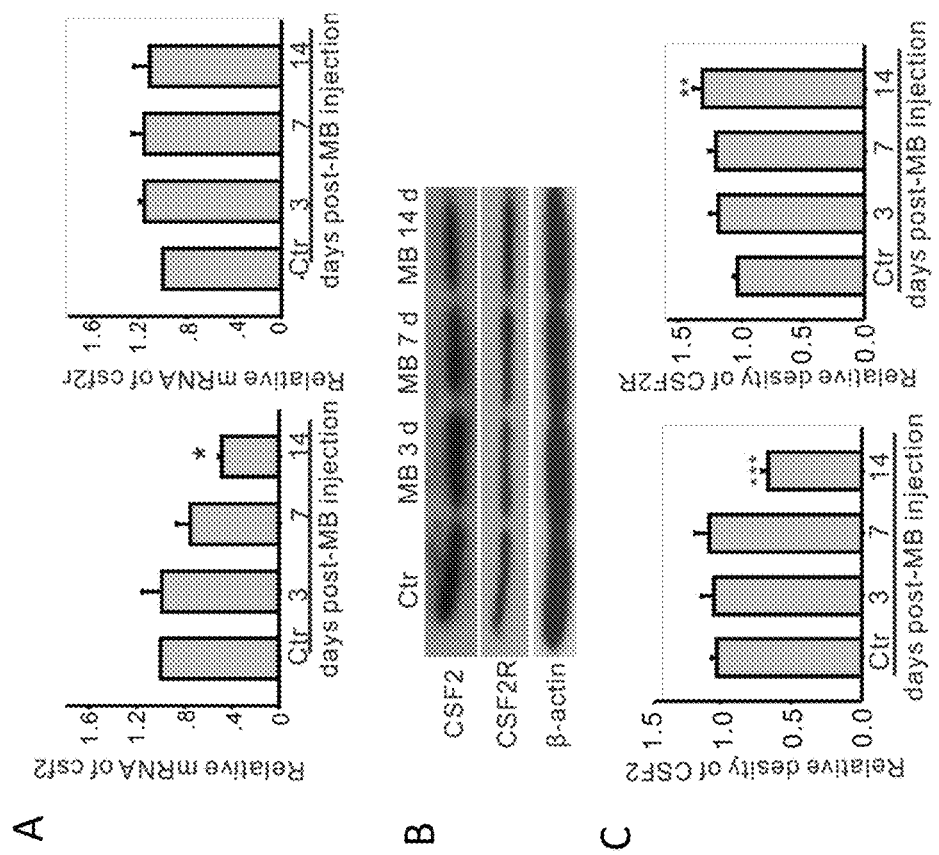
FIGS. 6A, 6B and 6C are a series of graphs and a Western blot demonstrating the downregulation of CSF2 expression in MB-injected mice. Results of qPCR (FIG. 6A) and Western blot (FIG. 6B, 6C) quantifications showing down-regulation of CSF2 and CSF2R expression in the mouse retinas after MB-induced elevation of intraocular pressure.
Figure 7:
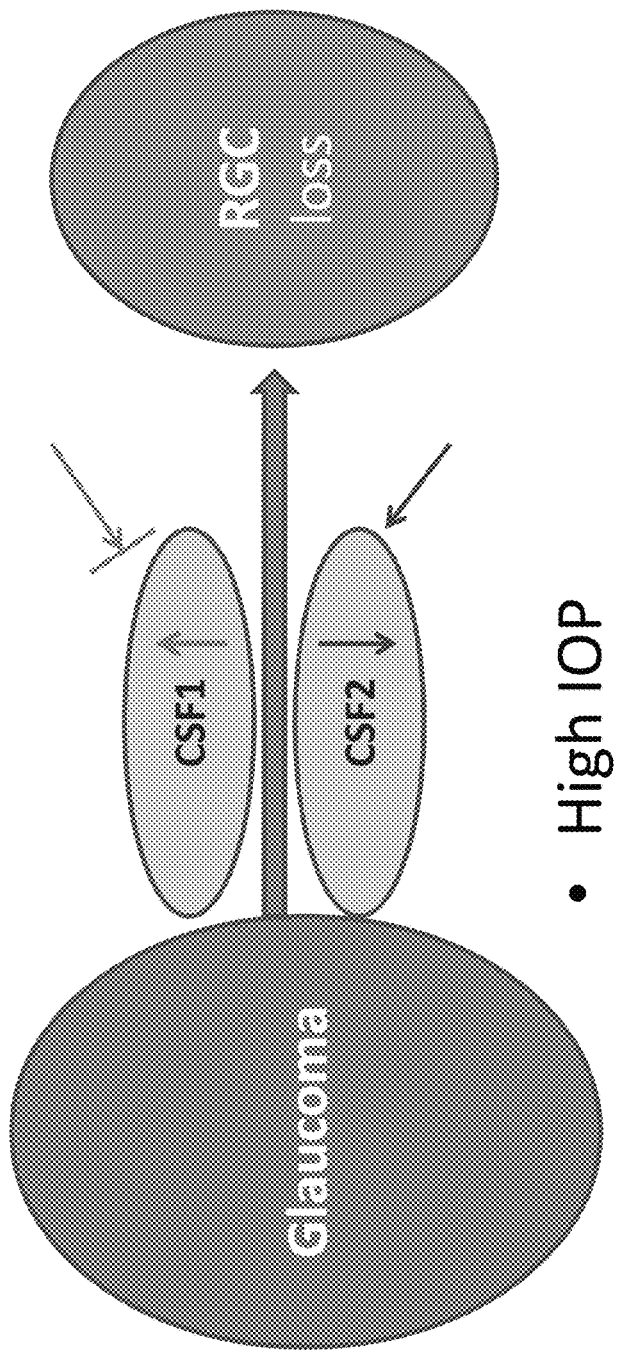
FIG. 7 is a schematic representation showing the experimental design. It was hypothesized that inhibiting CSF1 by administration of CSF1R antibody (CSF1R Ab) and/or promoting CSF2 signaling protect RGC against glaucomatous damage. Four experimental groups were proposed: following MB-injection to induce high IOP, mice received treatment of vehicle (PBS), CSF1R Ab, CSF2, or CSF1R Ab+CSF2 were studied.
Figure 8:
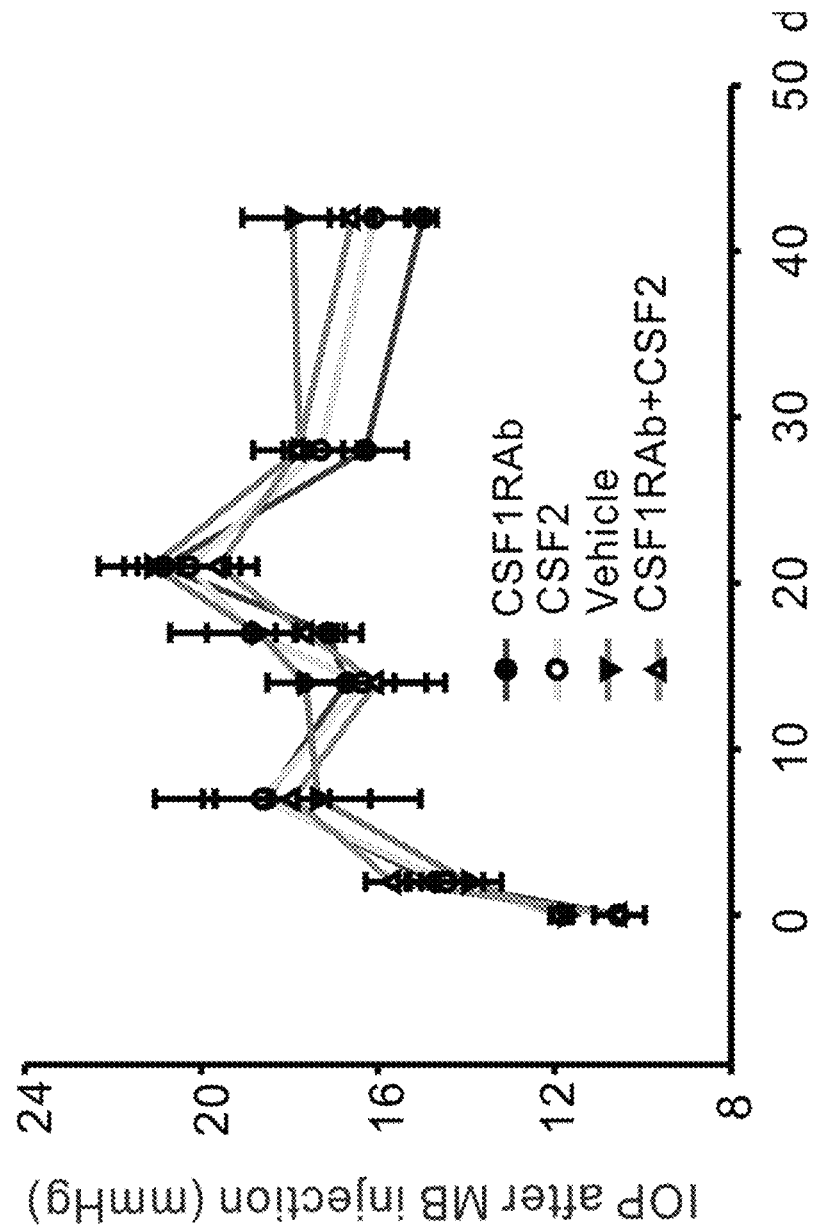
FIG. 8 is a graph showing the intraocular pressure (IOP) levels in all groups of mice. IOP levels were monitored during the entire period. IOP levels in all experimental groups were increased from 10 mmHg baseline to and maintained above 16 mmHg after MB injection.
Figure 9:
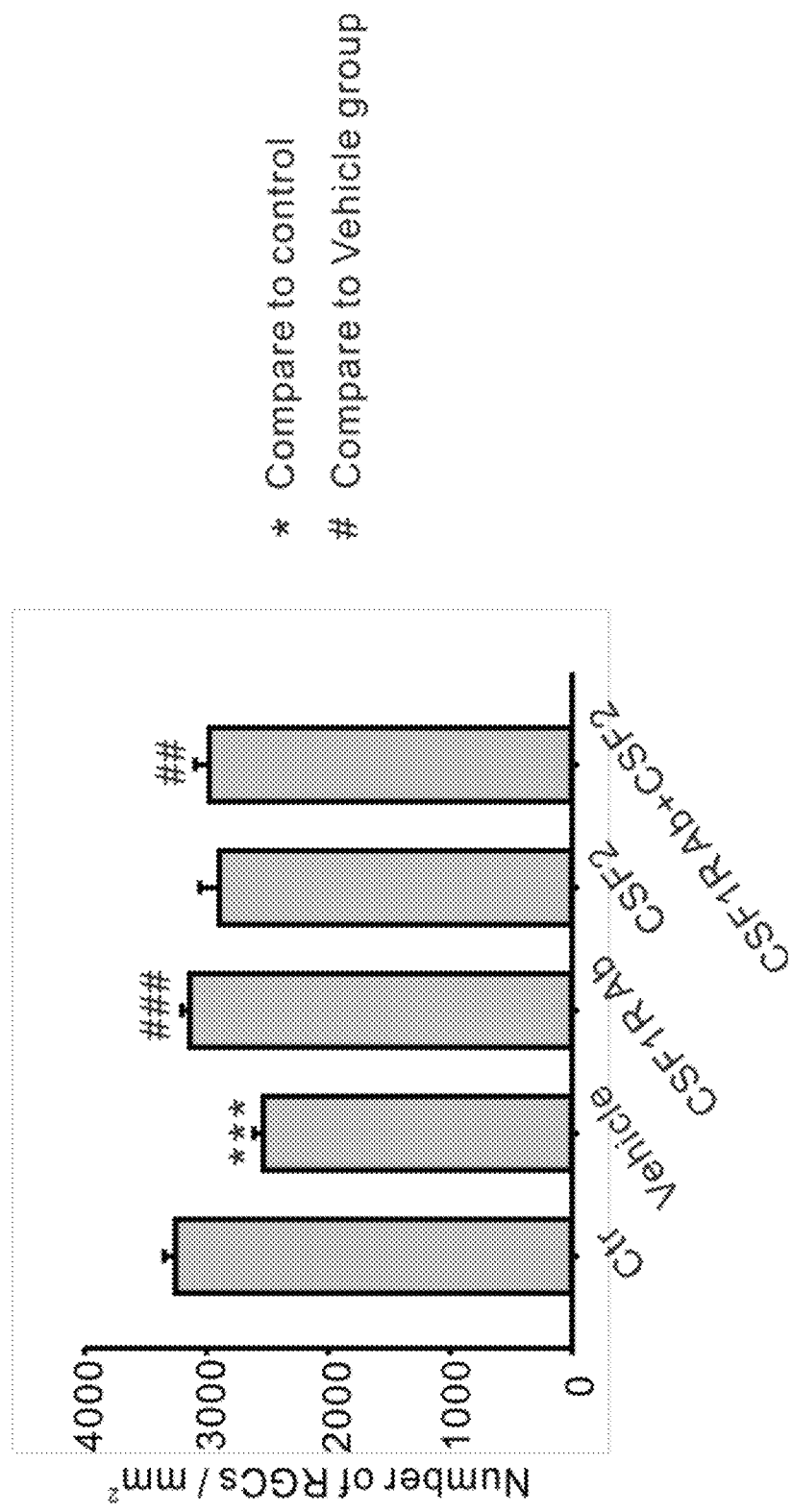
FIG. 9 is a graph showing decreased RGC loss by the treatment of CSF1RAb and/or CSF2 after MB injection. RGC counts from control (Ctr) mice and glaucomatous (MB-injected) mice received vehicle, CSF1RAb, CSF2 and CSF1RAb+CSF2 treatment.
Figure 10:
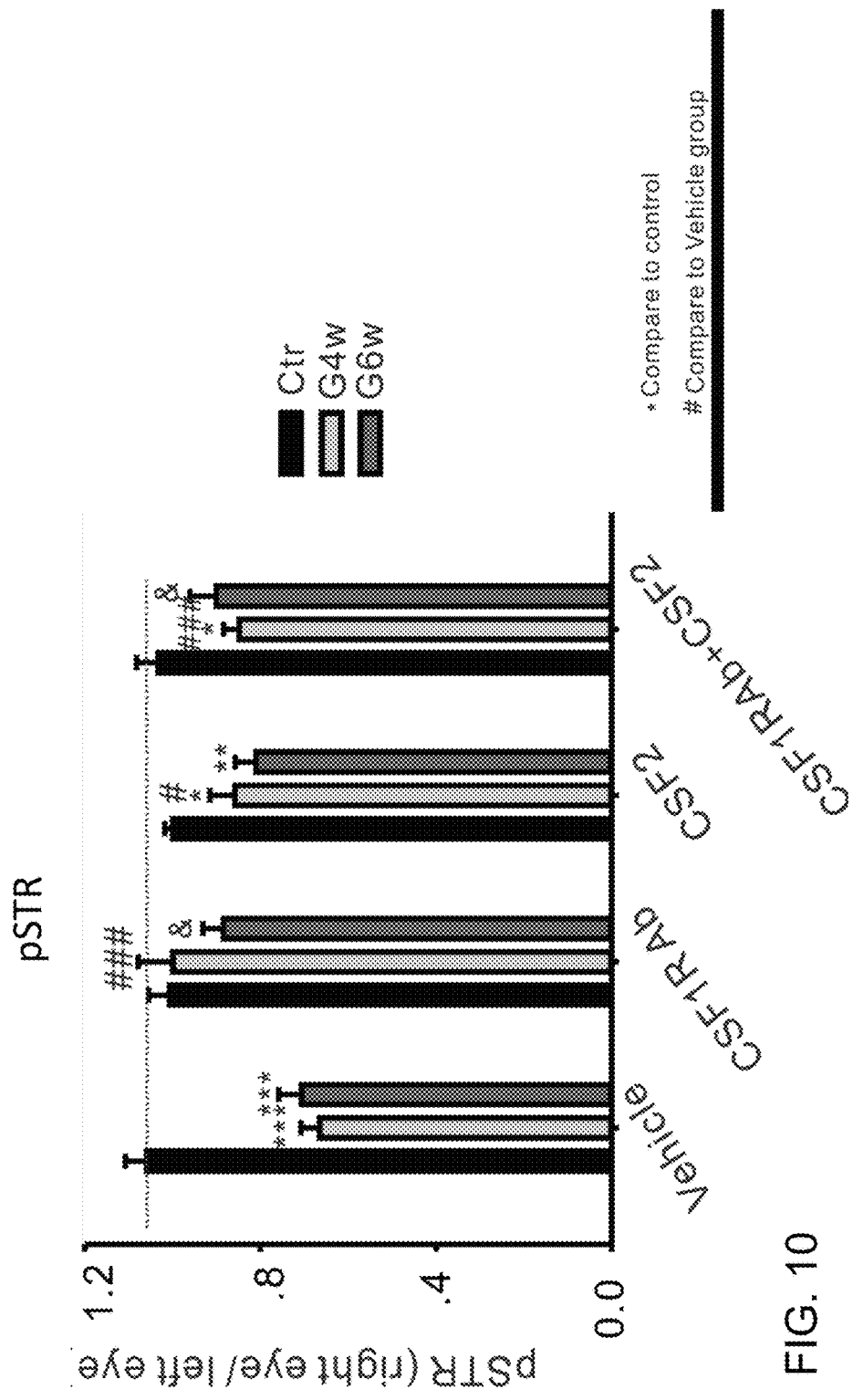
FIG. 10 is a graph showing that pSTR increased by treatment of CSF1RAb/CSF2 after MB injection. pSTR amplitudes assessed in MB-induced glaucomatous mice received vehicle, CSF1RAb, CSF2 or CSF1RAb+CSF2 treatment at before (Ctr), 4 (G4w) and 6 (G4w) weeks after MB injection.
Figures 11A, 11B:
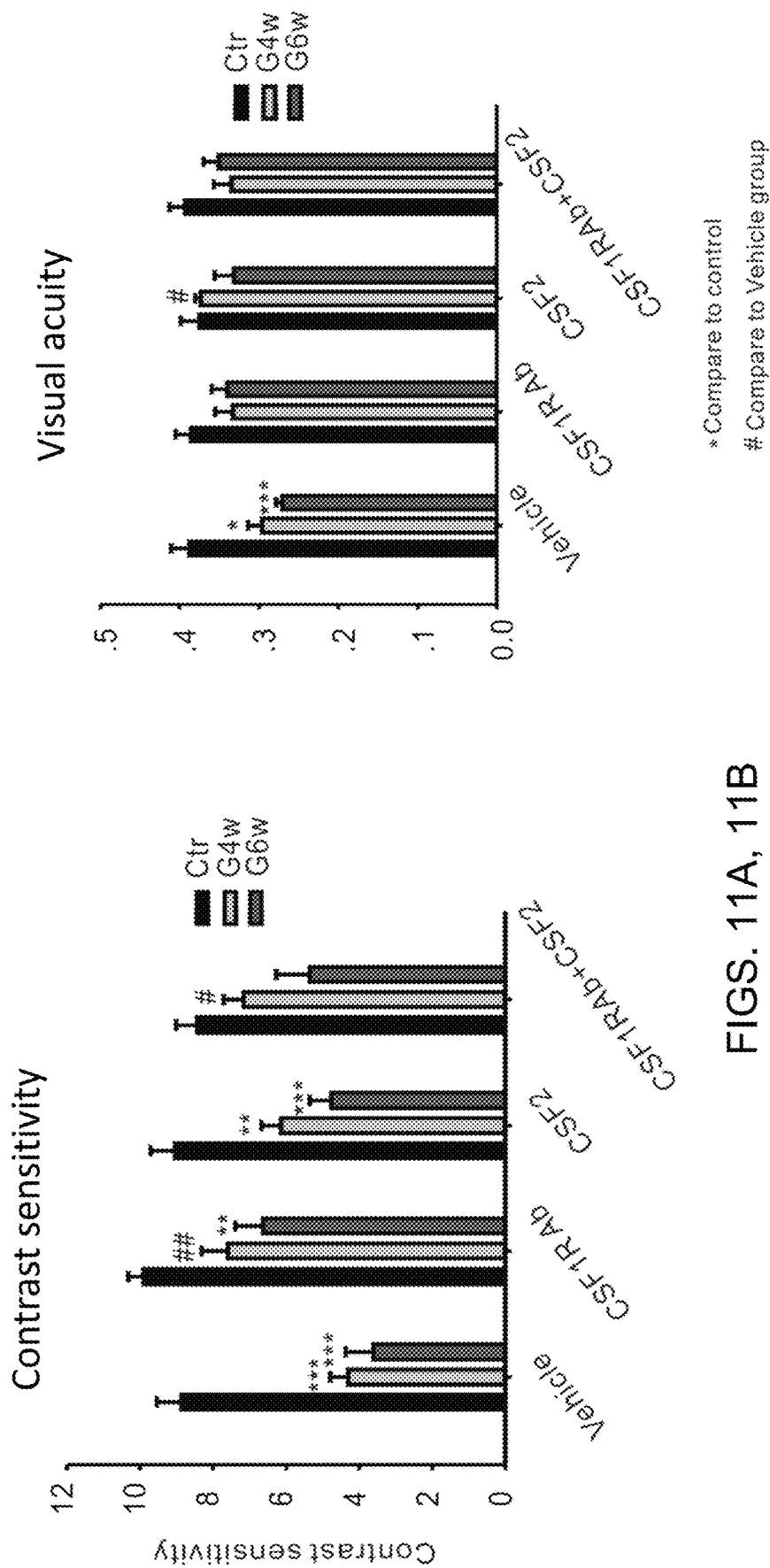

Activation of microglia plays a critical role in the progression of neurodegeneration in glaucoma. Colony stimulating factor 1 (CSF1) and colony stimulating factor 2 (CSF2) are involved in glaucomatous neuron loss by regulating microglia function. Mice with glaucoma showed upregulated CSF1 levels and downregulation of CSF2. Moreover, addition of CSF2 recombinant protein or neutralizing CSF1 by intravitreal injection of anti-CSF1 or antibody against CSF1 receptor in a glaucoma mouse model significantly suppressed microglial activation and protected the loss of retinal ganglion cells (RGCs) and vision function in a glaucoma mouse model. The data indicates that modulating CSF pathways is useful to confer a clinical benefit to subjects with glaucoma and/or optic neuropathy.

Colony Stimulating Factors

CSF-1 is present in the circulation, predominantly as the proteoglycan form, at biologically active concentrations of approximately 10 ng/mL. It is produced constitutively by a wide variety of cells of mesenchymal and epithelial origin. The level in the circulation increases in many different pathologies, including infections, cancer, and chronic inflammatory disease, regardless of etiology. CSF1 controls the survival, proliferation, and differentiation of mononuclear phagocytes and regulates cells of the females reproductive tract. CSF1 may also play an autocrine and/or paracrine role in cancers of the ovary, endometrium, breast, and myeloid and lymphoid tissues. CSF1 levels are also elevated in the circulation during pregnancy and contribute to placentation. In both mice and humans, there is a perinatal surge of tissue and circulating CSF1. In inflammation, CSF1 may also be produced by recruited macrophages themselves, although in the mouse at least, most macrophages do not produce CSF1 and undergo cell death in the absence of the protein. Under normal steady-state conditions, the production of CSF1 is balanced by its consumption by tissue macrophages, through receptor-mediated endocytosis by the CSF1 receptor (CSF1R) followed by intracellular destruction.

Granulocyte-macrophage colony-stimulating factor, also known as GM-CSF and CSF2, is a monomeric glycoprotein secreted by macrophages, T cells, mast cells, natural killer cells, endothelial cells and fibroblasts that functions as a cytokine. CSF2 controls the production, differentiation, and function of granulocytes and macrophages. The pharmaceutical analogs of naturally occurring CSF2 are called sargramostim and molgramostim. CSF2 can be used as a medication to stimulate the production of white blood cells following chemotherapy. It may also be used as a vaccine adjuvant in HIV-infected patients.

Colony-stimulating factor 3 (CSF 3), is a glycoprotein that stimulates the bone marrow to produce granulocytes and stem cells and release them into the bloodstream. Functionally, it is a cytokine and hormone, a type of colony-stimulating factor, and is produced by a number of different tissues. The pharmaceutical analogs of naturally occurring CSF3 are called filgrastim and lenograstim. CSF3 also stimulates the survival, proliferation, differentiation, and function of neutrophil precursors and mature neutrophils.

CSF1 and CSF2 play a primary role in mediating the actions of monocytes/macrophages, while CSF2 and CSF3 regulate granulocytes (neutrophils). Macrophages are polarized into M1 and M2 subtypes after activation. CSF2 promotes the M1 phenotype, which secretes pro-inflammatory cytokines, such as TNF-α and IL-12, and enhances the defense against bacteria or tumor by stimulating immune responses. In contrast, CSF1 stimulates the M2 phenotype that secretes anti-inflammatory cytokines and promotes tissue repair and angiogenesis.

The receptors of CSF1 and CSF2 belong to the tyrosine kinase family and activate the downstream pathways of PI-3/AKT, MAPK, STAT pathways to signal cell survival/proliferation, differentiation, and activation.

Prior to the invention, a role for CSF1 and/or CSF2 in glaucoma or retinal neurodegenerative disease had not been identified.

The data (FIGS. 1A-1D, FIGS. 2A-1D, FIGS. 3A-3F, FIGS. 5A, 5B, FIG. 9, FIG. 10, FIGS. 11A, 11B) showed that CSF1 or CSF1 receptor blockade, as well as CSF2 protein administration/augmentation protected retinal ganglion cell degeneration and protected visual performance in a mouse model of human glaucoma. These data unveil new insights into the pathogenesis of glaucomatous neural damage and demonstrate the therapeutic potential of blocking CSF1/CSF1 receptor activity and/or administration of CSF2 recombinant proteins via intravitreal injection for glaucomatous patients. Multiple injections of such agents into the vitreous are a common and low risk practice to patients in an ophthalmology clinic. Glaucoma is the most common form of optic neuropathy. The compositions and methods are also applicable to the treatment of other forms of optic neuropathy or for similar neurodegeneration conditions in the brain and spinal cord.

Regulation of Microglia Activation by CSFs Drives Neurodegeneration in Glaucoma

The studies described herein indicated that mice raised in the absence of microflora (germ-free mice) do not develop retinal ganglion cells (RGC) damage following elevation of intraocular pressure (TOP). Moreover, data indicated that the expression of colony stimulating factor 1 (CSF1) was downregulated, while CSF2 was upregulated in germ-free mice. Studies were then carried out to determine whether CSF1 and CSF2 played an opposing role mediating RGC loss in glaucoma. Herein, the expression and involvement of CSF1 and CSF2 in a standard mouse model of glaucoma, is reported.

Microbeads (MB) were injected into the anterior chamber of adult B6 mice to induce high IOP. The expression of CSF1/2 and their receptors was examined by immunostaining and quantitative polymerase chain reaction (qPCR) at different time points after MB injection. CSF2 and/or neutralizing antibody of CSF1 were adminstered intravitreally to mice with high IOP. Anti-brn3a staining was used to label RGC in the whole-mount retina.

The expression of CSF1 was found to be upregulated, while CSF2 was downregulated in the retina 2 weeks after MB injection. The data also showed that administration of either CSF2 or antibody specific for CSF1, e.g., a neutralizing antibody, reduced or attenuated glaucomatous RGC loss compared to saline-treated control mice. CSF1 receptor was found to associate with microglia and RGCs, while CSF2 receptor was expressed by Muller cells and RGCs.

These data indicate that CSF1 and CSF2 play opposing roles on microglia and Muller cells activation under elevated IOP that drive glaucomatous RGC degeneration. These findings indicate inhibition of CSF signaling and/or augmentation of CSF signaling is effective to reduce or prevent RGC loss and vision loss in subjects with a optic neuropathic disorder such as glaucoma.

CSF1, CSF2

UniProtKB—P09603 (CSF1 HUMAN) is provided below (SEQ ID NO: 1):

```
            10         20         30         40         50
    MTAPGAAGRC PPTTWLGSLL LLVCLLASRS ITEEVSEYCS HMIGSGHLQS 60         70         80         90        100
    LQRLIDSQME TSCQITFEFV DQEQLKDPVC YLKKAFLLVQ DIMEDTMRFR 110        120        130        140        150
    DNTPNAIAIV QLQELSLRLK SCFTKDYEEH DKACVRTFYE TPLQLLEKVK 160        170        180        190        200
    NVFNETKNLL DKDWNIFSKN CNNSFAECSS QDVVTKPDCN CLYPKAIPSS 210        220        230        240        250
    DPASVSPHQP LAPSMAPVAG LTWEDSEGTE GSSLLPGEQP LHTVDPGSAK 260        270        280        290        300
    QRPPRSTCQS FEPPETPVVK DSTIGGSPQP RPSVGAFNPG MEDILDSAMG 310        320        330        340        350
    TNWVPEEASG EASEIPVPQG TELSPSRPGG GSMQTEPARP SNFLSASSPL 360        370        380        390        400
    PASAKGQQPA DVTGTALPRV GPVRPTGQDW NHTPQKTDHP SALLRDPPEP 410        420        430        440        450
    GSPRISSLRP QGLSNPSTLS AQPQLSRSHS SGSVLPLGEL EGRRSTRDRR 460        470        480        490        500
    SPAEPEGGPA SEGAARPLPR FNSVPLIDTG HERQSEGSFS PQLQESVFHL 510        520        530        540        550
    LVPSVILVLL AVGGLLFYRW RRRSHQEPQR ADSPLEQPEG SPLTQDDRQV

ELPV
```

Human Colony Stimulating Factor 1 Receptor (CSF1-R) amino acid sequence AAH47521.1 is provided below (SEQ ID NO: 2):

```
      1 MGPGVLLLLL VATAWHGQGI PVIEPSVPEL

VVKPGATVEL RCVGNGSVEW DGPPSPHWTL

61 YSDGSSSILS TNNATFQNTG TYRCTEPGDP

LGGSAAIHLY VKDPARPWNV LAQEVVVFED

121 QDALLPCLLT DPVLEAGVSL VRVRGRPLMR

HTNYSFSPWH GETIHRAKFI QSQDYQCSAL

181 MGGRKVMSIS IRLKVQKVIP GPPALTLVPA

ELVRIRGEAA QIVCSASSVD VNFDVFLQHN
```

-continued
```
    241 NTKLAIHQQS DFHNNRYQKV LTLNLDQVDF

QHAGNYSCVA SNVQGKHSTS MFFRVVESAY

301 LNLSSEQNLI QEVTVGEGLN LKVMVEAYPG

LQGENWTYLG PFSDHQPEPK LANVTTKDTY

361 RHTFTLSLPR LKPSEAGRYS FLARNPGGWR

ALTFELTLRY PPEVSVIWTF INGSGTLLCA

421 ASGYPQPNVT WLQCSGHTDR CDEAQVLQVW

DDPYPEVLSQ EPFHKVTVQS LLTVETLEHN

481 QTYECRAHNS VGSGSWAFIP ISAGAHTHPP

DEFLFTPVVV ACMSIMALLL LLLLLLLYKY
```

-continued
```
    541 KQKPKYQVRW KIIESYEGNS YTFIDPTQLP

YNEKWEFPRN NLQFGKTLGA GAFGKVVEAT

601 AFGLGKEDAV LKVAVKMLKS TAHADEKESL

MSELKIMSHL GQHENIVNLL GACTHGGPVL

661 VITEYCCYGD LLNFLRRKAE AMLGPSLSPG

QDPEGGVDYK NIHLEKKYVR RDSGFSSQGV

721 DTYVEMRPVS TSSNDSFSEQ DLDKEDGRPL

ELRDLLHESS QVAQGMAFLA SKNCIHRDVA

781 ARNVLLTNGH VAKIGDFGLA RDIMNDSNYI

VKGNARLPVK WMAPESIFDC VYTVQSDVWS
```

```
841  YGILLWEIFS LGLNPYPGIL VNSKFYKLVK
     DGYQMAQPAF APKNIYSIMQ ACWALEPTHR
901  PTFQQICSFL QEQAQEDRRE RDYTNLPSSS
     RSGGSGSSSS ELEEESSSEH LTCCEQGDIA
961  QPLLQPNNYQ FC
```

SEQ ID NO: 2; GenBank Accession AAH47521.1, incorporated herein by reference. Exemplary landmark residues, domains, and fragments of CSF1-R include, but are not limited to residues 28-85 (Immunoglobulin like domain), residues 207-293 (Immunoglobulin like domain), residues 209-290 (Immunoglobulin like domain), residues 299-400 (Fourth immunoglobulin (Ig)-like domain of stem cell factor receptor (SCFR)), residues 401-495 (Immunoglobulin like domain), 542-914 (Protein Kinases, catalytic domain), or residues 588 to 591, 594, 596, 614, 616, 647, 663 to 666, 778, 782 . . . 783, 785, and 795 and 796 (ATP binding sites). A fragment of a CSF1-R protein is less than the length of the full length protein, e.g., a fragment is at least 3, 4, 5, 6, 7, 8, 9, 10, 20, 30, 40, 50, 100, 200 or more residues in length, but less than e.g., 972 residues in the case of CSF1-R above.

Human CSF1-R nucleic acid sequence BC047521.1 (start and stop codons underlined) (SEQ ID NO: 3):

```
   1 ggtggccttg cctagctaaa aggggaagaa gaggatcagc ccaaggagga ggaagaggaa
  61 aacaagacaa acagccagtg cagaggagag gaacgtgtgt ccagtgtccc gatccctgcg
 121 gagctagtag ctgagagctc tgtgccctgg gcaccttgca gccctgcacc tgcctgccac
 181 ttccccaccg aggccatggg cccaggagtt ctgctgctcc tgctggtggc cacagcttgg
 241 catggtcagg aatcccagt gatagagccc agtgtccccg agctggtcgt gaagccagga
 301 gcaacggtga ccttgcgatg tgtgggcaat ggcagcgtgg aatgggatgg cccccatca
 361 cctcactgga ccctgtactc tgatggctcc agcagcatcc tcagcaccaa caacgctacc
 421 ttccaaaaca cggggaccta tcgctgcact gagcctggag accccctggg aggcagcgcc
 481 gccatccacc tctatgtcaa agaccctgcc cggccctgga acgtgctagc acaggaggtg
 541 gtcgtgttcg aggaccagga cgcactactg ccctgtctgc tcacagaccc ggtgctggaa
 601 gcaggcgtct cgctggtgcg tgtgcgtggc cggcccctca tgcgccacac caactactcc
 661 ttctcgccct ggcatggctt caccatccac agggccaagt tcattcagag ccaggactat
 721 caatgcagtg ccctgatggg tggcaggaag gtgatgtcca tcagcatccg gctgaaagtg
 781 cagaaagtca tcccagggcc cccagccttg acactggtgc ctgcagagct ggtgcggatt
 841 cgaggggagg ctgcccagat cgtgtgctca gccagcagcg ttgatgttaa ctttgatgtc
 901 ttcctccaac acaacaacac caagctcgca atccatcaac aatctgactt tcataataac
 961 cgttaccaaa aagtcctgac cctcaacctc gatcaagtag atttccaaca tgccggcaac
1021 tactcctgcg tggccagcaa cgtgcagggc aagcactcca cctccatgtt cttccgggtg
1081 gtagagagtg cctacttgaa cttgagctct gagcagaacc tcatccagga ggtgaccgtg
1141 ggggagggc tcaacctcaa agtcatggtg gaggcctacc caggcctgca aggttttaac
1201 tggacctacc tgggaccctt ttctgaccac cagcctgagc ccaagcttgc taatgttacc
1261 accaaggaca catacaggca caccttcacc ctctctctgc ccgcctgaa gccctctgag
1321 gctggccgct actccttcct ggccagaaac ccaggaggct ggagagctct gacgtttgag
1381 ctcacccttc gataccccca gaggtaagc gtcatatgga cattcatcaa cggctctggc
1441 acccttttgt gtgctgcctc tgggtacccc cagcccaacg tgacatggct gcagtgcagt
1501 ggccacactg ataggtgtga tgaggcccaa gtgctgcagg tctgggatga cccatacct
1561 gaggtcctga gccaggagcc cttccacaag gtgacggtgc agagcctgct gactgttgag
1621 accttagagc acaaccaaac ctacgagtgc agggcccaca acagcgtggg gagtggctcc
1681 tgggccttca tacccatctc tgcaggagcc cacacgcatc cccggatga gttcctcttc
1741 acaccagtgg tggtcgcctg catgtccatc atggccttgc tgctgctgct gctcctgctg
1801 ctattgtaca agtataagca gaagccaag taccaggtcc gctggaagat catcgagagc
1861 tatgagggca acagttatac tttcatcgac cccacgcagc tgccttacaa cgagaagtgg
```

-continued

```
1921 gagttccccc ggaacaacct gcagtttggt aagaccctcg gagctggagc ctttgggaag 1981 gtggtggagg ccacggcctt tggtctgggc aaggaggatg ctgtcctgaa ggtggctgtg 2041 aagatgctga agtccacggc ccatgctgat gagaaggagt ccctcatgtc cgagctgaag 2101 atcatgagcc acctgggcca gcacgagaac atcgtcaacc ttctgggagc ctgtacccat 2161 ggaggccctg tactggtcat cacggagtac tgttgctatg gcgacctgct caactttctg 2221 cgaaggaagg ctgaggccat gctgggaccc agcctgagcc ccggccagga ccccgaggga 2281 ggcgtcgact ataagaacat ccacctcgag aagaaatatg tccgcaggga cagtggcttc 2341 tccagccagg gtgtggacac ctatgtggag atgaggcctg tctccacttc ttcaaatgac 2401 tccttctctg agcaagacct ggacaaggag gatggacggc ccctggagct ccgggacctg 2461 cttcacttct ccagccaagt agcccaggc atggccttcc tcgcttccaa gaattgcatc 2521 caccgggacg tggcagcgcg taacgtgctg ttgaccaatg gtcatgtggc caagattggg 2581 gacttcgggc tggctaggga catcatgaat gactccaact acattgtcaa gggcaatgcc 2641 cgcctgcctg tgaagtggat ggccccagag agcatctttg actgtgtcta cacggttcag 2701 agcgacgtct ggtcctatgg catcctcctc tcggagatct tctcacttgg gctgaatccc 2761 taccctggca tcctggtgaa cagcaagttc tataaactgg tgaaggatgg ataccaaatg 2821 gcccagcctg catttgcccc aaagaatata tacagcatca tgcaggcctg ctgggccttg 2881 gagcccaccc acagacccac cttccagcag atctgctcct tccttcagga gcaggcccaa 2941 gaggacagga gagagcggga ctataccaat ctgccgagca gcagcagaag cggtggcagc 3001 ggcagcagca gcagtgagct ggaggaggag agctctagtg agcacctgac ctgctgcgag 3061 caaggggata tcgcccagcc cttgctgcag cccaacaact atcagttctg ctgaggagtt 3121 gacgacaggg agtaccactc tcccctcctc caaacttcaa ctcctccatg gatggggcga 3181 cacggggaga acatacaaac tctgccttcg gtcatttcac tcaacagctc ggcccagctc 3241 tgaaacttgg aaggtgagg gattcagggg aggtcagagg atcccacttc ctgagcatgg 3301 gccatcactg ccagtcaggg gctgggggct gagccctcac ccccgcctc ccctactgtt 3361 ctcatggtgt tggcctcgtg tttgctatgc caactagtag aaccttcttt cctaatcccc 3421 ttatcttcat ggaaatggac tgactttatg cctatgaagt ccccaggagc tacactgata 3481 ctgagaaaac caggctcttt ggggctagac agactggcag agagtgagat ctccctctct 3541 gagaggagca gcagatgctc acagaccaca ctcagctcag gccccttgga gcaggatggc 3601 tcctctaaga atctcacagg acctcttagt ctctgcccta tacgccgcct tcactccaca 3661 gcctcacccc tcccaccccc atactggtac tgctgtaatg agccaagtgg cagctaaaag 3721 ttgggggtgt tctgcccagt cccgtcattc tgggctagaa ggcaggggac cttggcatgt 3781 ggctggccac accaagcagg aagcacaaac tcccccaagc tgactcatcc taactaacag 3841 tcacgccgtg ggatgtctct gtccacatta aactaacagc attaatacaa aaaaaaaaaa 3901 aaaa
```

The sequence of CSF2 (also known as GM-CSF is described in NP 000749.2 granulocyte-macrophage colony-stimulating factor precursor; hereby incorporated by reference in its entirety.) (SEQ ID NO: 4):

```
  1 MWLQSLLLLG TVACSISAPA RSPSPSTQPW
    EHVNAIQEAR RLLNLSRDTA AEMNETVEVI
 61 SEMFDLQEPT CLQTRLELYK QGLRGSLTKL
    KGPLTMMASH YKQHCPPTPE TSCATQIITF
121 ESFKENLKDF LLVIPFDCWE PVQE
```

Antibodies and Inhibitors of CSF1 and CSF1R

A humanized immunoglobulin (Ig) G2 monoclonal antibody (mAb) directed against the cytokine colony stimulating factor 1 (CSF1; CSF-1; macrophage colony-stimulating factor; M-CSF), with potential immunomodulating and antineoplastic activities, anti-CSF1 monoclonal antibody PD-0360324 targets, binds to and neutralizes CSF1. This prevents the binding of CSF1 to its receptor CSF1R (CD115; M-CSFR), which is expressed on various immune cells, such as monocytes and macrophages. This prevents CSF1R activation and CSF1R-mediated signaling in these cells, leading to inhibition of monocyte differentiation, blocking the activity of macrophages, and reducing their production of inflammatory mediators, which reduces inflammation. By blocking the activity and proliferation of CSF1R-dependent tumor-associated macrophages (TAMs) in the tumor microenvironment, PD-0360324 reduces TAM-mediated immune suppression, decreases regulatory T cells (Tregs), re-activates the immune system, and improves anti-tumor cell responses mediated by increasing infiltration by cytotoxic T cells. TAMs play key roles in immune suppression, and tumor cell proliferation and survival. CSF-1 plays a key role in the regulation of the proliferation, differentiation and survival of monocytes and macrophages.

Exemplary antibodies include those available from R&D systems (Minneapolis, MN), e.g., Mouse M-CSF Antibody neutralized; Cat #: MAB416-SP, or eBioscience (ThermoFischer); CD115 (c-fms) Monoclonal Antibody; Cat #: AFS9 or Peprotech (Rocky Hill, NJ 08553) United States; Recombinant Murine GM-CSF; Cat #: 315-03.

An orally bioavailable inhibitor of colony stimulating factor 1 receptor (CSF-1R; CSF1R), with potential antineoplastic activity, CSF1R inhibitor BLZ945 (4-[2((1R,2R)-2-hydroxycyclohexylamino)-benzotinazol-6-yloxyl]-pyridine-2-carboxylic acid methylamide) selectively binds to CSF1R expressed on tumor-associated macrophages (TAMs), blocks the activity of CSF1R, and inhibits CSF1R-mediated signal transduction pathways. This inhibits the activity and proliferation of TAMs, and reprograms the immunosuppressive nature of existing TAMs. Altogether, this reduces TAM-mediated immune suppression in the tumor microenvironment, re-activates the immune system, and improves anti-tumor cell responses mediated by T-cells. CSF1R, also known as macrophage colony-stimulating factor receptor (M-CSFR) and CD115 (cluster of differentiation 115), is a cell-surface receptor for its ligand, colony stimulating factor 1 (CSF1); this receptor is overexpressed by TAMs in the tumor microenvironment, and plays a major role in both immune suppression and the induction of tumor cell proliferation.

Another inhibitor of the tyrosine kinase receptor colony stimulating factor 1 receptor (CSF1R; CSF-1R; C-FMS; CD115; M-CSFR), with potential antineoplastic, macrophage checkpoint-inhibitory and immunomodulating activities, DCC-3014, targets and binds to CSF1R expressed on monocytes, macrophages, and osteoclasts and inhibits the binding of the CSF1R ligands colony-stimulating factor-1 (CSF-1) and interleukin-34 (IL-34), to CSF1R. This prevents CSF activation and CSF1R-mediated signaling in these cells. This blocks the production of inflammatory mediators by macrophages and monocytes and reduces inflammation. By blocking the recruitment to the tumor microenvironment and activity of CSF1R-dependent tumor-associated macrophages (TAMs), DCC-3014 inhibits the immunomodulating activity by macrophages and enhances T-cell infiltration and antitumor T-cell immune responses, which inhibits the proliferation of tumor cells. TAMs play key roles in the tumor microenvironment and allow for immune suppression; TAMs promote inflammation, tumor cell proliferation, angiogenesis, invasiveness and survival.

Examples of other inhibitors of CSF1 receptors undergoing clinical phase trials in cancer patients, include: Pexidartinib (PLX3397, PLX108-01), PLX7486, ARRY-382, JNJ-40346527, BLZ945, Emactuzumab (RG7155), AMG820, IMC-CS4 (LY3022855), MCS110, GW-2580, Gleevec (imatinib mesylate). (Cannarile, Michael A et al. "Colony-stimulating factor 1 receptor (CSF1R) inhibitors in cancer therapy" *Journal for immunotherapy of cancer* vol. 5, 1 53. 18 Jul. 2017, doi:10.1186/s40425-017-0257-y).

PLX73086 (AC708) which is a small molecule inhibitor of CSF1R, which leads to reduced CSF1R activation and may restore resistance to angiogenesis inhibition through a decrease in tumor associated macrophages (Lyons, Y. A. et al., *Oncotarget*. 2017 Aug. 24; 8(57):96496-96505. doi: 10.18632/oncotarget.20410. eCollection 2017 Nov. 14). Chiauranib (CS2164) is a multi-kinase inhibitor that inhibits AURKB, CSF-1R, VEGFRs, KIT, and PDGFRA, resulting in decreased tumor growth and angiogenesis (Zhou, Y. et al., *Cancer Set*. 2017 March; 108(3):469-477. doi: 10.1111/cas.13141. Epub 2017 Mar. 7). Sprycel (dasatinib) is an inhibitor of the SRC-family of protein kinases, BCR-ABL, and ABL, and has additional activity against other kinases including KIT, DDR1/2, PDGFRA/B, and EPHA2, which prevents cell growth (Kothiwale S. et al., *Drug Discov Today*. 2015 February; 20(2):255-61. doi: 10.1016/j.drudis.2014.09.025. Epub 2014 Oct. 7). DCC-3014 inhibits CSF1R, potentially resulting in increased anti-tumor immune response in combination with other agents (*Cancer Res* 2016; 76(14 Suppl):Abstract nr 4889). Debio 0617B is a multi-kinase inhibitor of SRC, JAK, and ABL, the class III kinases, CSF1R, FLT3, KIT, and PDGFR, and the class V kinases, VEGFR 1/2/3, which may result in inhibition of Stat3 and Stat5 signaling, leading to inhibition of tumor cell growth and metastasis (Murone, M. et al., *Mol Cancer Ther*. 2016 October; 15(10):2334-2343. Epub 2016 Jul. 20). Dovitinib (TKI258) targets multiple receptor tyrosine kinases including Flt3, c-Kit, CSF1R, FGFR 1-4, VEGFR 1-3, and PDGFR alpha and beta, potentially resulting in decreased tumor growth (Lesca E., et *J Mol Biol*. 2014 Nov. 11; 426(22):3744-3756. doi: 10.1016/j.jmb.2014.09.004. Epub 2014 Sep. 16; André F. et al., *Clin Cancer Res*. 2013 Jul. 1; 19(13):3693-702. doi: 10.1158/1078-0432.CCR-13-0190. Epub 2013 May 8). Emactuzumab (RG7155) is a monoclonal antibody that inhibits dimerization of CSF1R, resulting in decreased ligand-dependent and ligand-independent signaling (Ries C. H. et al., *Cancer Cell*. 2014 Jun. 16; 25(6):846-59. doi: 10.1016.j.ccr.2014.05.016. Epub 2014 Jun. 2). FF-10101 is a second generation and irreversible inhibitor of Flt3, including the internal tandem duplication (FLT3-ITD) and known resistance mutations (D835Y, Y842C, Y842H, or F691L) and also inhibits Kit and Csf1r (Fms) (Yamaura T. et al., *Blood*. 2018 Jan. 25; 131(4):426-438. doi: 10.1182/blood-2017-05-786657. Epub 2017 Nov. 29). GW2580 is an ATP-competitive selective inhibitor of CSF-1R, which may lead to decreased tumor cell growth (Ryder M. et al., PLoS One. 2013; 8(1):e54302. doi: 10.1371/journal.pone.0054302. Epub 2013 Jan. 23). JNJ-40346527 is a small molecule inhibitor of CSF1R (von Tresckow B. et al., *Clin Cancer Res*. 2015 Apr. 15; 21(8): 1843-50. doi: 10.1158/1078-0432.CCR-14-1845. Epub 2015 Jan. 27). Ki20227 inhibits CSF1R, which may result in decreased CSF-dependent cell growth (Ohno H. et al., *Mol Cancer Ther*. 2006 November; 5(11):2634-43). Lestaurtinib (CEP-701) (Hexner E. O. et al., *Blood*. 2008 Jun. 15; 111(12):5663-71. Epub 2007 Nov. 5). Linifanib (ABT-869) is a receptor tyrosine kinase inhibitor with specificity against FLT1 (VEGFR1), CSF-1R, KDR (VEGFR2), FLT3, and KIT, which may result in inhibition of cell proliferation and tumor growth, and tumor regression (Albert D. H. et al., *Mol Cancer Ther.* 2006 April; 5(4):995-1006). Rydapt (midostaurin) is a multi-kinase inhibitor (Ashman L. K. et al., *Expert Opin Investig Drugs.* 2013 January; 22(1):103-15. doi: 10.1517/13543784.2013.740010. Epub 2012 Nov. 6). Tasigna (nilotinib) inhibits several tyrosine kinases including BCR-ABL, PDGFR, KIT, DDR and CSF-1R (Blay J. Y. et al., *Semin Oncol.* 2011 April; 38 Suppl 1:S3-9. doi: 10.1053/j.seminoncol.2011.01.016). Pexidartinib (PLX3397) inhibits multiple receptor tyrosine kinases, including KIT, CSF1R, FLT3, and FLT3/ITD (Smith C. C. et al., *Cancer Discov.* 2015 June; 5(6):668-79. doi: 10.1158/2159-8290.CD-15-0060. Epub 2015 Apr. 6). PLX7486 binds to and inhibits CSF1R, TRKA, TRKB, and TRKC. Nexavar (sorafenib) is a multikinase inhibitor with activity against several kinases, including RAF kinases, VEGFR2, VEGFR3, PDGFR-beta, KIT, FLT3, RET, and CSF1R (Ullrich K. et al., *Br J Haematol.* 2011 November; 155(3):398-402. doi: 10.1111/j.1365-2141.2011.08685.x. Epub 2011 Apr. 22). Sutent (sunitinib) inhibits KDR (VEGFR2), PDGFR, c-KIT, FLT3, RET, and CSF1R (Subbiah V. et al., *J Hematol Oncol.* 2014 Aug. 1; 7:52. doi: 10.1186/s13045-014-0052-x).

In certain embodiments a CSF1R inhibitor comprises PLX3397 (Tahmasebi F. et al., *J Cell Biochem.* 2019 Jan. 10. doi: 10.1002jcb.28344), GW-2580 (Gerber Y. N. et al., *Front Cell Neurosci.* 2018; 12: 368.), BLZ-945 (Pyonteck S. M. et al., *Nat Med.* 2013 October; 19(10):1264-72. doi: 10.1038/nm.3337) or combinations thereof. In certain embodiments a CSF1R neutralizing antibody comprises: RG-7155, FPA-008, M279 (publication available, e.g., from AMGEN) or combinations thereof.

The antibodies which specifically bind to CSF1 or receptors thereof, inhibit the function or activity of the CSF1 molecule. The antibodies can be produced by any means known in the art directed to SEQ ID NOS: 1 or 2. In certain embodiments, the antibodies or fragments thereof, specifically bind to a CSF1 peptide or CSF1R having at least a 50% sequence identity to SEQ ID NOS: 1 or 2 respectively. In certain embodiments, the antibodies or fragments thereof, specifically bind to a CSF1 peptide or CSF1R having at least a 75% sequence identity to SEQ ID NOS: 1 or 2 respectively. In certain embodiments, the antibodies or fragments thereof, specifically bind to a CSF1 peptide or CSF1R having at least a 95% sequence identity to SEQ ID NOS: 1 or 2 respectively. In certain embodiments, the antibodies or fragments thereof specifically bind to epitopes in SEQ ID NOS: 1 or 2.

In certain embodiments, a CSF1 and receptor thereof inhibitor(s) preferentially inhibit CSF1 and receptors thereof, as compared to CSF2. In certain embodiments, a CSF1 inhibitor or a CSF1R inhibitor, inhibit the expression and/or activity and/or function of CSF1 by about 1-fold as compared to a CSF2 activity or function. In certain embodiments, a CSF1 inhibitor or a CSF1R inhibitor, inhibit the expression and/or activity and/or function of CSF1 by about 2-fold, 3-fold, 5-fold, 10-fold, 20-fold, 50-fold or more as compared to CSF2 activity or function. In certain embodiments, a CSF1 inhibitor or a CSF1R inhibitor, inhibit the expression and/or activity and/or function of CSF1 by at least 5% as compared to CSF2 activity or function. In certain embodiments, a CSF1 inhibitor or a CSF1R inhibitor, inhibit the expression and/or activity and/or function of CSF1 by at least 10%, 15%, 20%, 30%, 40%, 50%, 60%, 70%, 80%, 85%, 86%, 87%, 88%, 89%, 90%, 91%, 92%, 93%, 94%, 95%, 96%, 97%, 98%, 99%, or more as compared to CSF2 activity or function.

Figure 12:
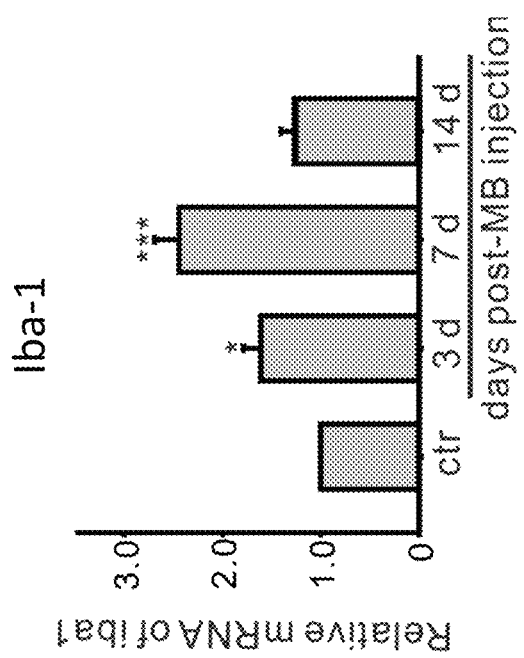
FIG. 12 is a graph showing that high IOP induced Iba-1 expression. qPCR quantification of Iba-1 levels in the retinas of mice at day 0, 3, 7, 14 after MB injection.
Figure 13:
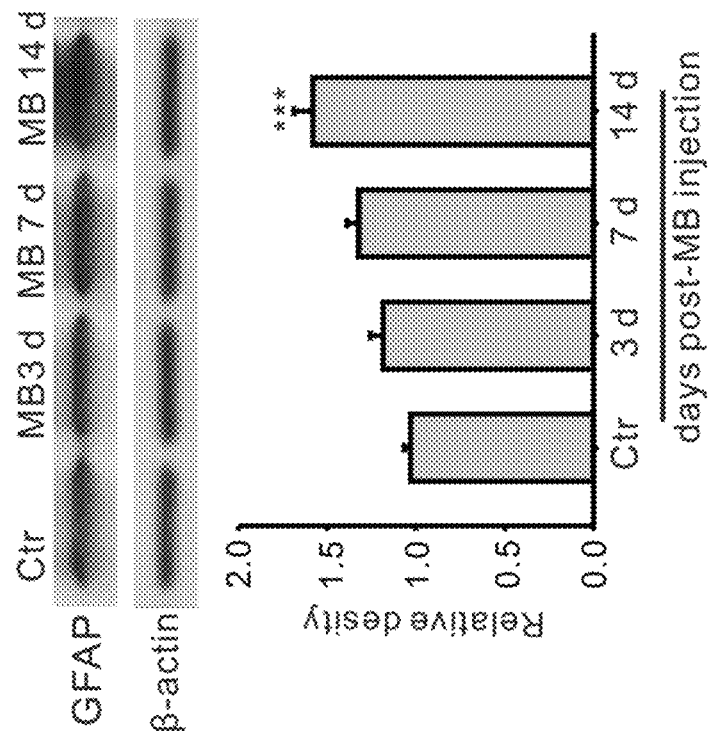
FIG. 13 is a Western blot and a graph demonstrating that high IOP activates Muller glia. Western blot quantification of the expression of activated Muller glia marker, GFPA, in the mouse retinas at day 0, 3, 7, 14 after MB injection.

The activity of CSF1 and CSF2 can be determined by any number of assays known in the art and also detailed herein. For example, mRNA expression, protein expression (FIGS. 1A-1C, FIGS. 2A-2D, FIGS. 5A-5B, FIGS. 6A-6C), intraocular pressure (FIGS. 3A-3G, FIG. 8, FIG. 12), cytokine profiles (FIGS. 5A, 5B), RGC loss (FIG. 9), positive scotopic threshold response (pSTR) (FIG. 10), visual function (FIGS. 11A, 11B), Iba-1 expression (FIG. 12), activation of Muller glia (FIG. 13). Whether an inhibitor specifically inhibits CSF1 or receptor thereof versus CSF2 can be determined by similar assays. For example, expression of CSF1, CSF1R versus CSF2. These assays can be combined with clinical examination which are routine.

The function of retinal ganglion cells (RGCs) can be non-invasively assessed in experimental and genetic models of glaucoma by means of variants of the ERG technique that emphasize the activity of inner retina neurons. The best understood technique is the Pattern Electroretinogram (PERG) in response to contrast-reversing gratings or checkerboards, which selectively depends on the presence of functional RGCs. In glaucoma models, the PERG can be altered before histological loss of RGCs; PERG alterations may be either reversed with moderate IOP lowering or exacerbated with moderate IOP elevation. Under particular luminance-stimulus conditions, the Flash-ERG displays components that may reflect electrical activity originating in the proximal retina and be altered in some experimental glaucoma models (positive Scotopic Threshold response, pSTR; negative Scotopic Threshold Response, nSTR; Photopic Negative Response, PhNR; Oscillatory Potentials, OPs; multifocal ERG, mfERG) (Vittorio Porciatti, *Exp Eye Res.* 2015 December; 141: 164-170).

In some embodiments, the antigen-binding domain is a humanized antibody of fragments thereof. A "humanized" antibody is an antibody in which all or substantially all complementarity determining region (CDR) amino acid residues are derived from non-human CDRs and all or substantially all framework region (FR) amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

In some embodiments, the heavy and light chains of an antibody can be full-length or can be an antigen-binding portion (a Fab, F(ab 1)2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

Among the provided antibodies are antibody fragments. An "antibody fragment" refers to a molecule other than an intact antibody that comprises a portion of an intact antibody that binds the antigen to which the intact antibody binds.

Examples of antibody fragments include but are not limited to Fv, Fab, Fab', Fab'-SH, F(ab')2; diabodies; linear antibodies; variable heavy chain (VH) regions, single-chain antibody molecules such as scFvs and single-domain VET single antibodies; and multispecific antibodies formed from antibody fragments. In particular embodiments, the antibodies are single-chain antibody fragments comprising a variable heavy chain region and/or a variable light chain region, such as scFvs.

In certain embodiments, the antibodies are single-domain antibodies. Single-domain antibodies are antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

In certain embodiments, the antibody or antibody fragments have high binding affinity for CSF1 or CSF1 receptors. In embodiments, the increased binding affinity is greater than effected by a reference antigen.

In certain embodiments, inhibitors of CSF1 are selected based on their ability to inhibit CSF1 expression or activity. In certain embodiments, the inhibitors of CSF1 are selected based on their ability to inhibit expression or function of the CSF1 receptor or inhibiting CSF1 from binding to CSF1 receptors. In certain embodiments, these potential therapeutic agents identified based on the screening assays are selected for testing their therapeutic activity. In certain embodiments, the therapeutic activity is suppression of microglial activation, protection against loss of retinal ganglion cells (RGCs) and vision function.

Candidate/Test Agents: Various candidate agents, e.g. inhibitors of CSF1 and receptor thereof, can be employed in the screening methods of the invention, including any naturally existing or artificially generated agents. They can be of any chemistry class, such as antibodies, small molecules, proteins, peptides, small organic compounds, saccharides, fatty acids, steroids, purines, pyrimidines, nucleic acids, and various structural analogs or combinations thereof. In some embodiments, the screening methods utilize combinatorial libraries of candidate agents. Combinatorial libraries can be produced for many types of compounds that can be synthesized in a step-by-step fashion. Such compounds include polypeptides, beta-turn mimetics, nucleic acids, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated herein by reference for all purposes). Peptide libraries can also be generated by phage display methods. See, e.g., Devlin, WO 91/18980.

Candidate agents include numerous chemical classes, though typically they are organic compounds including small organic compounds, nucleic acids including oligonucleotides, peptides or antibodies. Small organic compounds suitably may have e.g. a molecular weight of more than about 40 or 50 yet less than about 2,500. Candidate agents may comprise functional chemical groups that interact with proteins and/or DNA.

Candidate agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of e.g. bacterial, fungal and animal extracts are available or readily produced.

Chemical Libraries: Developments in combinatorial chemistry allow the rapid and economical synthesis of hundreds to thousands of discrete compounds. These compounds are typically arrayed in moderate-sized libraries of small molecules designed for efficient screening. Combinatorial methods can be used to generate unbiased libraries suitable for the identification of novel compounds. In addition, smaller, less diverse libraries can be generated that are descended from a single parent compound with a previously determined biological activity.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in a large number of combinations, and potentially in every possible way, for a given compound length (i.e., the number of amino acids in a polypeptide compound). Millions of chemical compounds can be synthesized through such combinatorial mixing of chemical building blocks.

A "library" may comprise from 2 to 50,000,000 diverse member compounds. Preferably, a library comprises at least 48 diverse compounds, preferably 96 or more diverse compounds, more preferably 384 or more diverse compounds, more preferably, 10,000 or more diverse compounds, preferably more than 100,000 diverse members and most preferably more than 1,000,000 diverse member compounds. By "diverse" it is meant that greater than 50% of the compounds in a library have chemical structures that are not identical to any other member of the library. Preferably, greater than 75% of the compounds in a library have chemical structures that are not identical to any other member of the collection, more preferably greater than 90% and most preferably greater than about 99%.

The preparation of combinatorial chemical libraries is well known to those of skill in the art. For reviews, see Thompson et al., Synthesis and application of small molecule libraries, Chem Rev 96:555-600, 1996; Kenan et al., Exploring molecular diversity with combinatorial shape libraries, Trends Biochem Sci 19:57-64, 1994; Janda, Tagged versus untagged libraries: methods for the generation and screening of combinatorial chemical libraries, Proc Natl Acad Sci USA. 91:10779-85, 1994; Lebl et al., One-bead-one-structure combinatorial libraries, Biopolymers 37:177-98, 1995; Eichler et al., Peptide, peptidomimetic, and organic synthetic combinatorial libraries, Med Res Rev. 15:481-96, 1995; Chabala, Solid-phase combinatorial chemistry and novel tagging methods for identifying leads, Curr Opin Biotechnol. 6:632-9, 1995; Dolle, Discovery of enzyme inhibitors through combinatorial chemistry, Mol. Divers. 2:223-36, 1997; Fauchere et al., Peptide and non-peptide lead discovery using robotically synthesized soluble libraries, Can J. Physiol Pharmacol. 75:683-9, 1997; Eichler et al., Generation and utilization of synthetic combinatorial libraries, Mol Med Today 1: 174-80, 1995; and Kay et al., Identification of enzyme inhibitors from phage-displayed combinatorial peptide libraries, Comb Chem High Throughput Screen 4:535-43, 2001.

Other chemistries for generating chemical diversity libraries can also be used. Such chemistries include, but are not limited to, peptoids (PCT Publication No. WO 91/19735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., Proc. Nat. Acad. Sci. USA, 90:6909-6913 (1993)); vinylogous polypeptides (Hagihara, et al., J. Amer. Chem. Soc. 114:6568 (1992)); nonpeptidal peptidomimetics with $\beta$-D-glucose scaffolding (Hirschmann, et al., J. Amer. Chem. Soc., 114:9217-9218 (1992)); analogous organic syntheses of small compound libraries (Chen, et al., J. Amer. Chem. Soc., 116:2661 (1994)); oligocarbamates (Cho, et al., Science, 261:1303 (1993)); and/or peptidyl phosphonates (Campbell, et al., J. Org. Chem. 59:658 (1994)); nucleic acid libraries (see, Ausubel, Berger and Sambrook, all supra); peptide nucleic acid libraries (see, e.g., U.S. Pat. No. 5,539, 083); antibody libraries (see, e.g., Vaughn, et al., Nature Biotechnology, 14(3):309-314 (1996) and PCT/US96/10287); carbohydrate libraries (see, e.g., Liang, et al., Science, 274:1520-1522 (1996) and U.S. Pat. No. 5,593,853); small organic molecule libraries (see, e.g., benzodiazepines, Baum C&E. News, January 18, page 33 (1993); isoprenoids (U.S. Pat. No. 5,569,588); thiazolidinones and metathiazanones (U.S. Pat. No. 5,549,974); pyrrolidines (U.S. Pat. Nos. 5,525,735 and 5,519,134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif, 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Bio sciences, Columbia, Md., etc.).

The screening assays of the invention suitably include and embody, animal models, cell-based systems and non-cell based systems. Identified genes, variants, fragments, or oligopeptides thereof are used for identifying agents of therapeutic interest, e.g. by screening libraries of compounds or otherwise identifying compounds of interest by any of a variety of drug screening or analysis techniques. The gene, allele, fragment, or oligopeptide thereof employed in such screening may be free in solution, affixed to a solid support, borne on a cell surface, or located intracellularly. The measurements will be conducted as described in detail in the examples section which follows.

In some embodiments, a method of identifying candidate therapeutic agents comprises screening a sample containing the specific target molecule in a high-throughput screening assay.

In another embodiment, a method of identifying therapeutic agents comprises contacting: (i) a target molecule with a candidate therapeutic agent; determining whether (i) the agent modulates a function of the peptide or interaction of the peptide with a partner molecule; or (ii) the agent modulates expression and/or function of the nucleic acid sequence of the target.

In another embodiment, a method of identifying candidate therapeutic agents for treatment of disease, comprises culturing an isolated cell expressing a target molecule, administering a candidate therapeutic agent to the cultured cell; correlating the target molecules expression, activity and/or function in the presence or absence of a candidate therapeutic agent as compared to control cells, wherein a drug is identified based on desirable therapeutic outcomes. For example, a drug which modulates levels of the target molecule whereby such levels are responsible for the disease state or the target molecule modulates the activity or amount of another molecule whether upstream or downstream in a pathway. In other examples the assays measure kinase activity. In other examples, the assay measure binding partners. In other examples, the assay measures amounts of candidate therapeutic agents which provide a desired therapeutic outcome.

Another suitable method for diagnosis and candidate drug discovery includes contacting a test sample with a cell expressing a target molecule, and detecting interaction of the test agent with the target molecule, an allele or fragment thereof, or expression product of the target molecule an allele or fragment thereof.

In another embodiment, a sample, such as, for example, a cell or fluid from a patient is isolated and contacted with a candidate therapeutic molecule. The genes, expression products thereof, are monitored to identify which genes or expression products are regulated by the drug.

Pharmaceutical Compositions

As described above, the compositions of the present invention can be prepared in a variety of ways known to one of ordinary skill in the art. Regardless of their original source or the manner in which they are obtained, the compositions of the invention can be formulated in accordance with their use. For example, the nucleic acids and vectors described above can be formulated within compositions for application to cells in tissue culture or for administration to a patient or subject. Any of the pharmaceutical compositions of the invention can be formulated for use in the preparation of a medicament, and particular uses are indicated below in the context of treatment. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer: intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intra-arterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

This invention also includes pharmaceutical compositions which contain, as the active ingredient, polypeptides, nucleic acids and vectors described herein in combination with one or more pharmaceutically acceptable carriers. The term pharmaceutically acceptable carrier, includes any and all solvents, dispersion media, coatings, antibacterial, isotonic and absorption delaying agents, buffers, excipients, binders, lubricants, gels, surfactants and the like, that may be used as media for a pharmaceutically acceptable substance. In making the compositions of the invention, the active ingredient is typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), lotions, creams, ointments, gels, soft and hard gelatin capsules, suppositories, sterile injectable solutions, and sterile packaged powders. As is known in the art, the type of diluent can vary depending upon the intended route of administration. The resulting compositions can include additional agents, such as preservatives. In some embodiments, the carrier can be, or can include, a lipid-based or polymer-based colloid. In some embodiments, the carrier material can be a colloid formulated as a liposome, a hydrogel, a microparticle, a nanoparticle, or a block copolymer micelle. As noted, the carrier material can form a capsule, and that material may be a polymer-based colloid.

In some instances, the topical ocular formulation is a solution, a suspension, creams, ointments, gels, gel-forming liquid, suspension containing liposomes or micelles, spray formulation, or an emulsion. In some cases, the topical ocular formulation also includes one or more pharmaceutically acceptable excipients selected from stabilizers, surfactants, polymer base carriers, gelling agents, organic co-solvents, pH active components, osmotic active components and with or without preservatives. In some cases, the sustained release semi-solid formulation, sustained release solid formulation or ocular implant is injected into the affected eye. In some embodiments, the sustained release semi-solid formulation, sustained release solid formulation or ocular implant further comprises a pharmaceutically acceptable excipient. In some cases, the sustained release semi-solid formulation, sustained release solid formulation or ocular implant includes a CSF1 or receptor thereof inhibitor, CSF2 polypeptide, or combinations thereof; and a biodegradable polymer selected from polylactic acid (PLA), polyglycolic acid (PLGA) and polylactic acid and polyglycolic acid copolymers.

The ophthalmic formulations further comprise at least one ophthalmically acceptable excipient such as, but not limited to, demulcent, tonicity adjusting agent, preservative, buffering agent, pH adjusting agent, solubilizing agent, surfactant, chelating agent, penetration enhancer, emulsifying agent, suspending agent, stabilizing agent, antioxidant, carrier, plasticizer, release modifying or controlling excipients, ion exchange resins and the like. Suitable demulcents include, but are not limited to, glycerin, polyvinyl pyrrolidone, polyethylene oxide, polyethylene glycol (PEG) such as but not limited to PEG 400, PEG 300 and the like or combinations thereof; propylene glycol, sorbitol and polyacrylic acid and the like or combinations thereof. Tonicity adjusting agents useful in the compositions of the present invention may include, but are not limited to, salts such as, but not limited to, sodium chloride, potassium chloride and calcium chloride, non-ionic tonicity agents may include, but are not limited to, propylene glycol, glycerol, mannitol, dextran and the like or combinations thereof.

Suitable chelating agents may include, but are not limited to, EDTA and its salts. Solubilizing agents, that may be employed include, but are not limited to, CREMOPHOR EL®, tween 80, cyclodextrin and the like or combinations thereof. Suitable cyclodextrins may be employed, such as, but not limited to, α-cyclodextrin, β-cyclodextrin γ-cyclodextrin, hydroxypropyl-β-cyclodextrin, hydroxypropyl-γ-cyclodextrin, dimethyl-β-cyclodextrin and dimethyl-γ-cyclodextrin, and the like or combinations thereof pH adjusting agents may include sodium hydroxide, hydrochloric acid, boric acid, Tris, triethanolamine and sodium hydroxide. Suitable buffering agents include, but are not limited to, phosphates, acetates and the like, and amino alcohols such as 2-amino-2-methyl-1-propanol (AMP), ascorbates, borates, hydrogen carbonate/carbonates, citrates, gluconates, lactates, propionates and TRIS (tromethamine) buffers, and the like or combinations thereof. Suitable preservatives include, but are not limited to, benzalkonium chloride, polyquatemium-1, p-hydroxybenzoic acid ester, sodium perborate, sodium chlorite, alcohols such as chlorobutanol, benzyl alcohol or phenyl ethanol, guanidine derivatives such as polyhexamethylene biguanide, sodium perborate, sorbic acid, and the like or combinations thereof. Suitable penetration enhancers that may optionally be employed include, but are not limited to, polyoxyethylene glycol lauryl ether, polyoxyethylene glycol stearyl ether, polyoxyethylene glycol oleyl ether, sodium taurocholate, saponins, CREMOPHOR EL, and the like or combinations thereof.

Suitable surfactants that may be employed include, but are not limited to, ionic and nonionic surfactants, and the like or combinations thereof. Suitable nonionic surfactants include, but are not limited to, poloxamers, tyloxapol, polysorbates, polyoxyethylene castor oil derivatives, sorbitan esters, polyoxyl stearates and a mixture of two or more thereof. Suitable pharmaceutical carriers include sterile water; electrolytes such as sodium chloride; dextrose; dextrose in water or saline; lower alkanols, ointment bases such as but not limited to, natural wax e.g. white bees wax, camauba wax, wool wax (wool fat), purified lanolin, anhydrous lanolin; petroleum wax e.g. solid paraffin, microcrystalline wax; hydrocarbons e.g. liquid paraffin, white petrolatum (e.g. white PROTOPET®), yellow petrolatum, and the like or combinations thereof. Suitable emulsifying agent may be included such as, but not limited to, mono- or di-glyceride of a fatty acid, phosphatide, e.g., lecithin, polysorbates, macrogols, poloxamers, tyloxapol, polyethylene glycol derivatives, polyvinyl alcohol and the like, and mixtures thereof. Suitable stabilizing agent such as, but not limited to, polyethylene glycol hydroxystearate, thiourea, thiosorbitol, sodium dioctyl sulfosuccinate, monothioglycerol and the like, or combinations thereof may be employed. Antioxidants such as, but not limited to, ascorbic acid, acetylcysteine, cysteine, sodium hydrogen sulfite, butylated hydroxyanisole, butylated hydroxytoluene or alpha-tocopherol acetate may be employed. Plasticizers, such as, but not limited to, glycerol, and the like may be employed.

Release modifying or controlling excipients, such as but not limited to, polymeric release modifying or controlling excipients, non-polymeric release modifying or controlling excipients or combinations thereof may be included in the compositions of the present invention. Exemplary release modifying or controlling excipients include glyceryl behenate, chitosan, carrageenan, cellulose derivatives such as ethylcellulose, acrylic acid and methacrylic acid polymers or copolymers and the like, or derivatives or combinations thereof. The ophthalmic formulations of the present invention may optionally include additional viscosity enhancing agents such as, but not limited to, cellulose and cellulose derivatives, such as, but not limited to, methylcellulose, hydroxypropylcellulose, hydroxyethyl cellulose, ethylhydroxyethyl cellulose, hydroxypropylmethylcellulose, sodium carboxymethylcellulose, cellulose acetophthalate, and the like or combinations thereof; alginic acid, sodium alginate, propylene glycol alginate, polyvinylpyrrolidone, carboxyvinyl polymers or carbomers (CARBOPOL®), polyvinyl alcohol, glycerin, polyethylene glycol, triblock copolymers of polyoxypropylene and polyoxyethylene, polyethoxylated sorbitan, polysorbate 80, chondroitin sulfate, dimethicone, perfluorononyl dimethicone, cyclomethicone, dextrans, proteoglycans, natural polysaccharides, such as, but not limited to, hyaluronic acid and salts thereof, guar gum, karaya, xyloglucan gum, chitosan, gellan gum, pectin, collagen, modified collagen and like or combinations thereof.

The ophthalmic formulations of the present invention may optionally include additional gelling agents such as, but not limited to, polysaccharide gums such as, but not limited to, gellan gum, tamarind gum, tragacanth, locust bean gum, agarose, carageenans, guar gum, hydroxypropyl guar gum, hyaluronic acid, chitosan, konjac, acacia, pectin, arabic, curdlan, glucan gum, scleroglucan and sulfated glucan sulfate and the like or combinations thereof; cellulose and its derivatives such as, but not limited to, methyl cellulose, carboxymethyl cellulose, methyl cellulose, hydroxypropyl cellulose, methyl hydroxypropyl cellulose, hydroxypropyl methyl cellulose, cellulose acetate, ethyl cellulose, methyl hydroxyethyl cellulose, hydroxyethyl cellulose, cellulose gum, and the like or combinations thereof; cross-linked acrylic polymers or carbomer (CARBOPOL™), aloe vera gel, polyvinyl alcohol, polyacrylamide, poloxamer, polymethylvinylether-maleic anhydride, swellable water-insoluble polymers such as, but not limited to, hydrogel and the like or combinations thereof. Ion exchange resins such as, but not limited to, inorganic zeolites or synthetically produced organic resins may be employed in the compositions of the present invention. The ophthalmic formulations of the present invention may optionally include additional mucodhesive agents such as, but not limited to, polyaciylic acid, hyaluronans, chitosan, pullulan, cellulose derivatives such as, but not limited to, methyl cellulose, hydroxypropyl methyl cellulose, sodium carboxymethylcellulose, poly (galacturonic) acid, sodium alginate, pectin, xyloglucan, xanthan gum, carbomers (CARBOPOL™), polyvinyl alcohol, polyvinylpyrrolidone, polyethylene glycol, poloxamer, and the like or combinations thereof.

The above listing of examples is given for illustrative purposes and is not intended to be exhaustive. Examples of other agents useful for the foregoing purposes are well known in ophthalmic formulation and are contemplated by the present invention. It is also contemplated that the concentrations of the excipients in the formulations of the present invention can vary. The ophthalmic formulations of the present invention can be in the form of eye drops, eye lotions, suspensions, dispersions, gels, ointments, emulsions, colloidal solutions, ocular inserts, ocular hydrogels, films, minitablets, nanoemulsions, and particulate systems such as but not limited to, liposomes, microparticles, nanoparticles, and the like. In one embodiment, the ophthalmic formulation of the present invention is in the form of an in-situ gelling system. In another embodiment, the in-situ type gelling composition of the present invention may comprise one or more cross-linking agent, such as but not limited to borate, and the like. In another embodiment, the in-situ type gelling composition of the present invention does not comprise one or more cross-linking agent.

In a further embodiment, the ophthalmic formulation of the present invention in the form of ocular insert is a bioerodible ocular insert. In another embodiment, the ophthalmic formulation of the present invention in the form of ocular insert is a non-bioerodible ocular insert.

The ophthalmic formulations of the present invention may be in the form of liquid, solid or semisolid dosage form. Further, in one embodiment, the ophthalmic formulations of the present invention are formulated so as to have a pH and osmolality that are compatible with the eye. The ophthalmic formulations of the present invention may comprise depending on the final dosage form suitable ophthalmically acceptable excipients. In one embodiment, the ophthalmic formulations are formulated to maintain a physiologically tolerable pH range. In one embodiment, the pH range of the ophthalmic formulation is in the range of from 5 to 9. In another embodiment, pH range of the ophthalmic formulation is in the range of from 6 to 8.

In a further embodiment, the ophthalmic formulations of the present invention are for topical administration to the eye. In another embodiment, the ophthalmic formulations of the present invention are for intraocular or periocular administration. In a further embodiment, the ophthalmic formulations of the present invention are for immediate release of active agent in the ocular cavity.

In another embodiment, the ophthalmic formulations of the present invention are for sustained or controlled release in the ocular cavity. In a further embodiment, the ophthalmic formulations of the present invention are for at once-a-day administration. In one embodiment, the sustained or controlled release delivery of the active agent from the ophthalmic formulation is for a sustained period of time of about 24 hours. In another embodiment, the sustained or controlled release delivery of the active agent from the ophthalmic formulation is for a sustained period of time of about 12 hours. In a further embodiment, the sustained or controlled release delivery of the active agent from the ophthalmic formulation is for a sustained period of time of about 10 hours. In yet another embodiment, the sustained or controlled release delivery of the active agent from the ophthalmic formulation is for a sustained period of time of about 8 hours. In one embodiment, the sustained or controlled release delivery of the active agent from the ophthalmic formulation is for a sustained period of time of about 6 hours. In a further embodiment, the sustained or controlled release delivery of the active agent from the ophthalmic formulation is for a sustained period of time of about 4 hours to about 24 hours.

Depending on the dosage form of the ophthalmic formulations of the present invention, appropriate method of preparation is employed. Various methods for preparation of ophthalmic formulations known in the art may be employed. Further depending on the dosage form, the ophthalmic formulations or excipients and/or active agents employed therein are suitably sterilized by one or more methods known to a person skilled in the art. In one embodiment, the ophthalmic formulations of the present invention in the form of ocular insert, is prepared by molding or extrusion procedures well known in the art. In another embodiment, the ophthalmic formulation of the present invention in the form of ophthalmic solution is prepared by either by dissolving or suspending prescribed amount of a drug in a prescribed volume of a carrier solvent along ophthalmically acceptable excipients. Particle size of certain ophthalmic formulations of the present invention is within ophthalmically acceptable limits known to a person skilled in the art.

The compositions of the present invention are useful for the treatment of humans or animals.

Administration of a composition or formulation can be once a day, twice a day, three times a day, four times a day or more often. Frequency may be decreased during a treatment maintenance phase of the treatment, e.g., once every second or third day instead of every day or twice a day. The dose and the administration frequency can be adjusted based on the judgment of the treating physician, for example, taking into account the clinical signs, pathological signs and clinical and subclinical symptoms of a disease of the conditions treated with the present methods, as well as the patient's clinical history.

It will be appreciated that the amount of an agent disclosed herein required for use in treatment will vary with the route of administration, the nature of the condition for which treatment is required, and the age, body weight and condition of the patient, and will be ultimately at the discretion of the attendant physician. Compositions will typically contain an effective amount of a CSF1 or receptor thereof inhibitor, CSF2 polypeptide, or combinations thereof. Preliminary doses can be determined according to animal tests, and the scaling of dosages for human administration can be performed according to art-accepted practices.

Length of treatment, i.e., number of days, will be readily determined by a physician treating the subject; however, the number of days of treatment may range from about 1 day to about 365 days. As provided by the present methods, the efficacy of treatment can be monitored during the course of treatment to determine whether the treatment has been successful, or whether additional (or modified) treatment is necessary.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). Dosage forms for the CSF1 and CSF1R inhibitors, and CSF2 can be readily determined by the ordinarily skilled artisan, and can e.g., be obtained in animal models and in clinical studies reported in the literatures, for determining dosage, safety and efficacy according to standard methods known in the art. The exact formulation, route of administration and dosage can be chosen by the individual physician in view of the patient's condition.

In certain embodiments, the pharmaceutical composition comprises an anti-CSF1 antibody and a CSF2 recombinant peptide. In certain embodiments, the pharmaceutical composition comprises an anti-CSF1 receptor antibody and a CSF2 recombinant peptide. In certain embodiments, the pharmaceutical composition comprises an anti-CSF1 antibody and an anti-CSF1 receptor antibody. In certain embodiments, the pharmaceutical composition comprises an anti-CSF1 antibody, an anti-CSF1 receptor antibody and a CSF2 polypeptide. In certain embodiments, the pharmaceutical composition comprises an inhibitor of CSF1 antibody and/or an inhibitor of CSF1 receptor and/or a CSF2 polypeptide.

In certain embodiments, a pharmaceutical composition comprises a therapeutically effective amount of an inhibitor of colony stimulating factor-1 (CSF1) or a receptor thereof and a colony stimulating factor-2 (CSF2) protein or polypeptide. In certain embodiments, the inhibitor of CSF1 or a receptor thereof, comprises antibodies, antibody fragments, aptamers, small molecules, antisense oligonucleotides, siRNA reagents, Fab, Fab', F(ab')2 fragments, Fv fragments, single chain antibodies, antibody mimetics, peptoids, cytokines, cytokine agonists, cytokine antagonists, cellular factors, enzymes or combinations thereof.

In certain embodiments, the pharmaceutical compositions embodied herein, include cytokines, cytokine agonists, cytokine antagonist or combinations thereof. For example, a pharmaceutical composition comprises a therapeutically effective amount of an inhibitor of colony stimulating factor-1 (CSF1) or a receptor thereof and/or a colony stimulating factor-2 (CSF2) protein or polypeptide and/or a cytokine(s), cytokine agonists, cytokine antagonists or combinations thereof.

In certain embodiments, a CSF1 or CSF1 receptor inhibitors are formulated for ocular administration. In certain embodiments, a CSF1 inhibitor is formulated for ocular administration. In certain embodiments, a CSF2 polypeptide or protein formulated for ocular administration.

In some examples, the inhibitor or polypeptide is administered intravitreally. Exemplary inhibitors of CSF1 or CSF receptor include antibody specific for CSF1 or a CSF1 receptor. For example, a CSF1 inhibitor formulated for ocular administration.

Alternatively or in conjunction with CSF1 treatment, the therapy includes a CSF2 polypeptide or protein formulated for ocular administration.

The present invention provides formulations of inhibitors of CSF1, CSF1R, CSF2 polypeptides or combinations thereof, formed as a solution with viscosity similar to water. The solution includes pharmaceutically acceptable agents/excipients, for example, without being limiting, cyclodextrin. The solution thus formed is clear and colorless solution, suitable for topical administration to the eye.

The solutions of the present invention reduce anterior segment exposure of the active agent; thereby they allow increased concentration of the active agent in the solution and increased frequency of delivery, thus, promoting maintained high concentration of the active agent in the posterior segment of the eye.

The solutions of the invention comprise about 0.005% to about 95% w/v of the active agent of inhibitors of CSF1, CSF1R, CSF2 polypeptides or combinations thereof, or a pharmaceutically acceptable salt thereof. In some embodiments, the concentration of inhibitors of CSF1, CSF1R, CSF2 polypeptides or combinations thereof, in the solutions is about 0.005%-0.01%, about 0.01%-0.05%, about 0.05%-0.1%, about 0.1%-0.2%, about about 0.3%-0.4%, about 0.4%-0.5%, about 0.5%-0.6%, about 0.6%-0.7%, about about 0.8%-0.9%, about 0.9%-1.0%, about 1.0%-2.0%, about 2.0%-3.0%, about 3.0%-4.0%, about 4.0%-5.0%, 0.005%-20%, about 0.005%-%-25%, about 0.005%-30%, about 0.005%-40%, about 0.005%-50% or greater w/v for topical administration. In some embodiments, the solutions include about 0.005%, 0.05%, 0.1%, 0.2%, 0.3%, 0.4%, 0.5%, 0.7%, 0.8%, 0.9%, 1.0%, 2.0%, 3.0%, 4.0%, 5.0%, 10%, 15%, 20%, 25%, 30%, 40%, 50% or greater w/v of inhibitors of CSF1, CSF1R, CSF2 polypeptides or combinations thereof.

In some embodiments, the formulation comprises cyclodextrin for improving solubility of any of the inhibitors. Compound-I. Cyclodextrin, an oligosaccharide made up of six to eight dextrose units joined through one or four bonds increases solubility of active agents that have poor or low solubility in water or aqueous solutions (e.g., in PBS buffer). Cyclodextrins form hydrophilic complexes with hydrophobic active agents.

One or more cyclodextrins can be used are used in the solution of the present invention. Non-limiting examples of cyclodextrins for use in formulation of the current invention are, for example: 2-hydroxypropyl-β-cyclodextrin, methyl-β-cyclodextrin, randomly methylated-β-cyclodextrin, ethylated-.beta.-cyclodextrin, triacetyl-β-cyclodextrin, peracetylatedll-cyclodextrin, carboxymethyl-O-cyclodextrin, hydroxyethyl-β-cyclodextrin, 2-hydroxy-3-(trimethylammonio)propyl-.beta.-cyclodextrin, glucosyl-β-cyclodextrin, maltosyl-β-cyclodextrin, sulfobutyl ether-.beta.-cyclodextrin, branched-β-cyclodextrin, hydroxypropyl-γcyclodextrin, randomly methylated-γ-cyclodextrin, trimethyl-γ-cyclodextrin, or combinations thereof.

Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the singular forms "a," "an," and "the" include the plural reference unless the context clearly dictates otherwise. Thus, for example, a reference to "a disease," "a disease state", or "a nucleic acid" is a reference to one or more such embodiments, and includes equivalents thereof known to those skilled in the art and so forth.

As used herein, the term "about" in the context of a numerical value or range means±10% of the numerical value or range recited or claimed, unless the context requires a more limited range.

As used herein, the term "agent" is meant to encompass any molecule, chemical entity, composition, drug, therapeutic agent, chemotherapeutic agent, or biological agent capable of preventing, ameliorating, or treating a disease or other medical condition. The term includes small molecule compounds, antisense oligonucleotides, siRNA reagents, antibodies, antibody fragments bearing epitope recognition sites, such as Fab, Fab', F(ab')2 fragments, Fv fragments, single chain antibodies, antibody mimetics (such as DARPins, affibody molecules, affilins, affitins, anticalins, avimers, fynomers, Kunitz domain peptides and monobodies), peptoids, aptamers, enzymes, peptides organic or inorganic molecules, natural or synthetic compounds and the like. An agent can be assayed in accordance with the methods of the invention at any stage during clinical trials, during pre-trial testing, or following FDA-approval.

The term "antibody" herein is used in the broadest sense and includes polyclonal and monoclonal antibodies, including intact antibodies and functional (antigen-binding) antibody fragments, including fragment antigen binding (Fab) fragments, F(ab')2 fragments, Fab' fragments, Fv fragments, recombinant IgG (rIgG) fragments, variable heavy chain (Vu) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD. The term "antibody" is inclusive of all species, including human and humanized antibodies and the antigenic target, can be from any species. Thus, an antibody, for example, which binds to an antigen "X" can be mouse anti-human X, human anti-human X; humanized anti-human X, goat anti-human X; goat anti-mouse X; rat anti-human X; mouse anti-rat X and the like. The combinations of antibody generated in a certain species against an antigen target, e.g. "X", from another species, or in some instances the same species (for example, in autoimmune or inflammatory response) are limitless and all species are embodied in this invention.

"Aptamers" are DNA or RNA molecules that have been selected from random pools based on their ability to bind other molecules. The aptamer binds specifically to a target molecule wherein the nucleic acid molecule has sequence that comprises a sequence recognized by the target molecule in its natural setting. Alternately, an aptamer can be a nucleic acid molecule that binds to a target molecule wherein the target molecule does not naturally bind to a nucleic acid. The target molecule can be any molecule of interest. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art (see, e.g., Gold et al., Anna. Rev. Biochem. 64:763, 1995; Brody and Gold, J. Biotechnol. 74:5, 2000; Sun, *Curr. Opin. Mol. Ther.* 2:100, 2000; Kusser, *J. Biotechnol.* 74:27, 2000; Hermann and Patel, Science 287:820, 2000; and Jayasena, *Clinical Chem.* 45:1628, 1999).

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A "comparison window" refers to a segment of any one of the number of contiguous positions (e.g., least about 10 to about 100, about 20 to about 75, about 30 to about 50, 100 to 500, 100 to 200, 150 to 200, 175 to 200, 175 to 225, 175 to 250, 200 to 225, 200 to 250) in which a sequence may be compared to a reference sequence of the same number of contiguous positions after the two sequences are optimally aligned. In various embodiments, a comparison window is the entire length of one or both of two aligned sequences. In some embodiments, two sequences being compared comprise different lengths, and the comparison window is the entire length of the longer or the shorter of the two sequences. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

In various embodiments, an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 may be used, with the parameters described herein, to determine percent sequence identity for nucleic acids and proteins. Software for performing BLAST analyses is publicly available through the National Center for Biotechnology Information, as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The transitional tem) "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

As used herein, the term "cytokine" refers generically to proteins released by one cell population that act on another cell as intercellular mediators or have an autocrine effect on the cells producing the proteins. Examples of such cytokines include lymphokines, monokines; interleukins ("ILs") such as IL-1, IL-1α, IL-2, IL-3, IL-4, IL-5, IL-6, IL-7, IL-8, IL-9, IL-10, IL-11, IL-12, IL-13, IL-15, IL-17A-F, IL-18 to IL-29 (such as IL-23), IL-31, including PROLEUKIN™ rIL-2; a tumor-necrosis factor such as TNF-α or TNF-β, TGF-β1-3; and other polypeptide factors including leukemia inhibitory factor ("LIF"), ciliary neurotrophic factor ("CNTF"), cytokine ("CLC"), cardiotrophin ("CT"), and kit ligand ("KL").

As used herein, "effective" when referring to an amount of a therapeutic compound refers to the quantity of the compound that is sufficient to yield a desired therapeutic response without undue adverse side effects (such as toxicity, irritation, or allergic response) commensurate with a reasonable benefit/risk ratio when used in the manner of this disclosure.

"Excipient" is used herein to include any other compound that may be contained in or combined with one or more of the disclosed inhibitors or CSF2 polypeptides that is not a therapeutically or biologically active compound. As such, an excipient should be pharmaceutically or biologically acceptable or relevant (for example, an excipient should generally be non-toxic to the subject). "Excipient" includes a single such compound and is also intended to include a plurality of excipients. For the purposes of the present application the term "excipient" and "carrier" are used interchangeably throughout the description of the present application and said terms are defined herein as, "ingredients which are used in the practice of formulating a safe and effective pharmaceutical composition."

The term "high affinity" for an antibody refers to an antibody having a $K_D$ of $1 \times 10^{-7}$ M or less, more preferably $5 \times 10^{-8}$ M or less, even more preferably $1 \times 10^{-8}$ M or less, even more preferably $5 \times 10^{-9}$ M or less and even more preferably $1 \times 10^{-9}$ M or less for a target antigen. However, "high affinity" binding can vary for other antibody isotypes. For example, "high affinity" binding for an IgM isotype refers to an antibody having a $K_D$ of $10^{-6}$ M or less, $10^{-7}$ M or less, $10^{-8}$ M or less.

The term "identical" or percent "identity," in the context of two or more nucleic acids or polypeptide sequences, refer to two or more sequences or subsequences that are the same or have a specified percentage of amino acid residues or nucleotides that are the same (e.g., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire polypeptide sequence or an individual domain thereof), when compared and aligned for maximum correspondence over a comparison window, or designated region as measured using a sequence comparison algorithm or by manual alignment and visual inspection. Such sequences that are at least about 80% identical are said to be "substantially identical." In some embodiments, two sequences are 100% identical. In certain embodiments, two sequences are 100% identical over the entire length of one of the sequences (e.g., the shorter of the two sequences where the sequences have different lengths). In various embodiments, identity may refer to the complement of a test sequence. In some embodiments, the identity exists over a region that is at least about 10 to about 100, about 20 to about 75, about 30 to about 50 amino acids or nucleotides in length. In certain embodiments, the identity exists over a region that is at least about 50 amino acids in length, or more preferably over a region that is 100 to 500, 100 to 200, 150 to 200, 175 to 200, 175 to 225, 175 to 250, 200 to 225, 200 to 250 or more amino acids in length.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. A purified or isolated protein or peptide is free of amino acids or amino acid sequences that flank it its naturally-occurring state. Purified also defines a degree of sterility that is safe for administration to a human subject, e.g., lacking infectious or toxic agents. Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

As used in this specification and the appended claims, the term "or" is generally employed in its sense including "and/or" unless the content clearly dictates otherwise.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. For sequence comparison, typically one sequence acts as a reference sequence, to which test sequences are compared. In various embodiments, when using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

By "reference" is meant a standard or control condition.

A "small molecule" is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

As used herein, an antibody that "specifically binds" to a target is intended to refer to a targeting ligand, e.g. an antibody that binds to a target with a $K_D$ of $1 \times 10^{-7}$ M or less, more preferably $5 \times 10^{-8}$ M or less, more preferably $3 \times 10^{-8}$ M or less, more preferably $1 \times 10^{-8}$ M or less, even more preferably $5 \times 10^{-9}$ M or less.

The terms "subject," "patient," "individual," and the like as used herein are not intended to be limiting and can be generally interchanged. That is, an individual described as a "patient" does not necessarily have a given disease, but may be merely seeking medical advice. The term "subject" as used herein includes a subject diagnosed with an optic neuropathy. For example, the subject has been diagnosed with an elevated IOP. Alternatively, the subject is characterized as comprising an optic neuropathy in the absence of elevated IOP. In some instances, early glaucoma is characterized by aberrant CSF1 and/or CSF2 levels in the absence of elevated TOP. Such patients benefit from early treatment using the compositions and methods described herein.

As used herein, a "symptom" associated with a disorder includes any clinical or laboratory manifestation associated with the disorder, and is not limited to what the subject can feel or observe.

As used herein, "treating" encompasses, e.g., inhibition, regression, or stasis of the progression of a disorder. Treating also encompasses the prevention or amelioration of any symptom or symptoms of the disorder. As used herein, "inhibition" of disease progression or a disease complication in a subject means preventing or reducing the disease progression and/or disease complication in the subject.

The term "variable region" or "variable domain", when used in reference to an antibody, such as an antibody fragment, refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a VII or $V_L$ domain from an antibody that binds the antigen to screen a library of complementary $V_L$ or $V_H$ domains, respectively. See, e.g., Portolano et al., *J. Immunol.* 150: 880-887 (1993); Clarkson et al., *Nature* 352:624-628 (1991).

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, which in some embodiments relate to mammalian nucleic acid and amino acid sequences, are intended to encompass homologous and/or orthologous genes and gene products from other animals including, but not limited to other mammals, fish, amphibians, reptiles, and birds. In preferred embodiments, the genes, nucleic acid sequences, amino acid sequences, peptides, polypeptides and proteins are human.

Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for preventing visual function loss in a subject with glaucoma, comprising intravitreally administering to the subject a neutralizing antibody that specifically binds colony stimulating factor-1 receptor (CSF1R).

2. The method of claim 1, wherein the antibody specifically binds a portion of CSF1R.

3. The method of claim 1, wherein the antibody specifically binds a portion of SEQ ID NO: 1 or 2.

4. The method of claim 1, wherein the antibody is administered at least once a day.

5. The method of claim 1, wherein the antibody is administered once every second or third day.

6. The method of claim 1, wherein the antibody inhibits or reduces the binding of a CSF1R ligand to CSF1R.

7. The method of claim 6, wherein the CSF1R ligand is CSF1 or IL-34.

8. The method of claim 1, wherein the antibody comprises antibody fragments, Fab, Fab', F(ab')2 fragments, Fv fragments, single chain antibodies, humanized antibodies, or combinations thereof.

9. The method of claim 1, wherein the antibody comprises RG-7155, FPA-008, M279, or combinations thereof.

10. A method for improving visual function in a subject with glaucoma, comprising intravitreally administering to the subject a neutralizing antibody that specifically binds colony stimulating factor-1 receptor (CSF1R).

11. The method of claim 10, wherein the antibody specifically binds a portion of CSF1R.

12. The method of claim 10, wherein the antibody specifically binds a portion of SEQ ID NO: 1 or 2.

13. The method of claim 10, wherein the antibody is administered at least once a day.

14. The method of claim 10, wherein the antibody is administered once every second or third day.

15. The method of claim 10, wherein the antibody inhibits or reduces the binding of a CSF1R ligand to CSF1R.

16. The method of claim 15, wherein the CSF1R ligand is CSF1 or IL-34.

17. The method of claim 10, wherein the antibody comprises antibody fragments, Fab, Fab', F(ab')2 fragments, Fv fragments, single chain antibodies, humanized antibodies, or combinations thereof.

18. The method of claim 10, wherein the antibody comprises RG-7155, FPA-008, M279, or combinations thereof.

* * * * *